US007496456B2

(12) United States Patent
Hiyama et al.

(10) Patent No.: US 7,496,456 B2
(45) Date of Patent: Feb. 24, 2009

(54) 3D ULTRASONOGRAPHIC DEVICE

(75) Inventors: Kazuo Hiyama, Kanagawa-ken (JP);
Takahiro Ikeda, Kanagawa-ken (JP);
Motohisa Abe, Ibaraki-ken (JP);
Hirokazu Karasawa, Kanagawa-ken
(JP); Masahiro Katayama, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 11/587,482

(22) PCT Filed: Apr. 25, 2005

(86) PCT No.: PCT/JP2005/007816

§ 371 (c)(1),
(2), (4) Date: Jul. 30, 2007

(87) PCT Pub. No.: WO2005/103675

PCT Pub. Date: Nov. 3, 2005

(65) Prior Publication Data

US 2007/0282543 A1 Dec. 6, 2007

(30) Foreign Application Priority Data

Apr. 26, 2004 (JP) ............................. 2004-130390
Apr. 26, 2004 (JP) ............................. 2004-130391

(51) Int. Cl.
*G06F 3/01* (2006.01)
(52) U.S. Cl. ............................. 702/39; 702/48; 702/54; 702/55; 702/56
(58) Field of Classification Search .................. 702/39, 702/156, 179, 182, 183, 186, 48, 54, 55; 73/579; 600/454, 464; 700/132
See application file for complete search history.

(56) References Cited

U.S. PATENT DOCUMENTS 5,176,165 A * 1/1993 Traylor .................... 137/216.1
7,044,913 B2 * 5/2006 Shiki ......................... 600/454

(Continued)

FOREIGN PATENT DOCUMENTS

JP          5-094762 U          12/1993

(Continued)

*Primary Examiner*—Eliseo Ramos Feliciano
*Assistant Examiner*—Felix E Suarez
(74) *Attorney, Agent, or Firm*—Foley & Lardner LLP

(57) ABSTRACT

A three-dimensional ultrasonic inspection apparatus includes: a sensing device for ultrasonic inspection including an ultrasonic sensor as a transducer, in which a plurality of piezoelectric vibrators are disposed in a matrix or an array; a drive element selecting unit for selecting and driving a piezoelectric vibrator for producing an ultrasonic wave among the ultrasonic transducer; a signal detecting circuit for detecting the electric signal of the reflected echo by receiving the reflected echo from the joined area; a signal processing unit for subjecting the electric signal to signal processing and generating three-dimensional imaging data by causing the electric signals to correspond to mesh elements in a three-dimensional imaging region of the object to be inspected; and a display processing device for displaying the detection results and three-dimensional image data from the signal processing unit, while detecting the size and the position of the molten-solidified portion, and the size and the position of the weld defect of the joined area, from the intensity distribution of the three-dimensional imaging data generated by the signal processing unit.

20 Claims, 10 Drawing Sheets

U.S. PATENT DOCUMENTS 7,243,547 B2 * 7/2007 Cobianu et al. ............... 73/579

FOREIGN PATENT DOCUMENTS

| JP | 6-011495 A | 1/1994 |
| --- | --- | --- |
| JP | 6-265529 A | 9/1994 |
| JP | 7-218476 A | 8/1995 |
| JP | 8-304362 A | 11/1996 |
| JP | 11-326287 A | 11/1999 |
| JP | 2003-149213 A | 5/2003 |
| JP | 2003149213 A * | 5/2003 |
| JP | 2004-053360 A | 2/2004 |
| JP | 2004053360 A * | 2/2004 |
| WO | WO 2005/103675 A1 | 3/2005 |

* cited by examiner

3D ULTRASONOGRAPHIC DEVICE

TECHNICAL FIELD

The present invention relates to a three-dimensional ultrasonic inspection apparatus which performs non-destructive inspection of an inner structure, the state of joined area, and the state of a defect of an object to be inspected, using ultrasonic waves, and more specifically, relates to a three-dimensional ultrasonic inspection apparatus including a sensing device for the ultrasonic inspection, used for an ultrasonic imaging apparatus that three-dimensionally visualizes the state of a welded portion and the state of a weld defect of the object to be inspected.

BACKGROUND ART

An example of technologies that perform non-destructive inspection of the state of a welded portion and the state of a weld defect of a joined area between plate-like structures, an object to be inspected, is an ultrasonic test technology.

As an example of the ultrasonic inspection apparatuses employing the ultrasonic test technology, there is provided an ultrasonic inspection apparatus described in Japanese Unexamined Patent Application Publication Nos. 2003-149213 and 2004-53360.

In the ultrasonic inspection apparatus, an ultrasonic transducer, including a large number of piezoelectric vibrators disposed in a matrix, is used for production and detection of an ultrasonic wave. When a welded portion of an object to be inspected is subjected to imaging processing, the ultrasonic wave produced by the piezoelectric vibrators of the ultrasonic transducer is made incident on the welded portion, which is an joined area of the object to be inspected, a reflection echo of the ultrasonic wave reflected by the welded portion is received by the ultrasonic transducer, an electric signal corresponding to the received reflection echo is sent to a signal processing unit through a signal detecting circuit, and the echo signal is subjected to a parallel arithmetic processing in the signal processing unit. In the ultrasonic inspection apparatus, an ultrasonic image of the welded portion, subjected to image processing, is displayed on a display device so that, by means of visual inspection of the ultrasonic image, the states of the welded portion and a weld defect can be inspected without being destroyed.

In the known ultrasonic inspection apparatus, the states of a welded portion and a weld defect are inspected without being destroyed (in a non-destructive manner), by irradiating the welded portion of the object to be inspected with an ultrasonic wave, by performing imaging processing on the reflected echo to display an ultrasonic image on a display device, and by examining the displayed image of the welded portion by means of viewing.

Specifically, as described in Japanese Unexamined Patent Application Publication No. 11-326287, when a plate-like structure is the object to be inspected, and two plate-like structures are superposed and joined together by means of spot welding, by inspecting the states of the welded portion between the two plate-like structures and a weld defect using the ultrasonic inspection apparatus, in a non-destructive manner, it is possible to inspect whether a molten-solidified portion exists in the welded portion or not, and the presence or absence of the weld defect such as a blowhole, and the state of the weld defect.

Moreover, from Japanese Unexamined Patent Application Publication No. 6-265529, it is known that the bonding strength of the welded portion of the object to be inspected depends on the size of the molten-solidified portion, and the boundary between the joined area and the molten-solidified portion formed on the inner side thereof can be obtained from the inflexion point of the strength distribution curve of a reflection echo at the bottom portion of the joined area of the object to be inspected.

In the known ultrasonic inspection apparatus, a layer structure of an object to be inspected having a plurality of different acoustic properties, and defects, voids, and peelings of the welded portion of the object to be inspected can be visualized by means of an ultrasonic wave, and examined by viewing of the ultrasonic image of a welded portion displayed on the display device. However, since a two-dimensional ultrasonic image has been examined by means of viewing, fluctuations in the examination results has been occurred due to differences in opinion between individual examiners, and it has been difficult to quantitatively inspect the positional relationship of the welded portion with respect to the object to be inspected, correctly and accurately in three dimensions. In other words, the known ultrasonic inspection apparatus has the following problems.

1. Since internal inspection of the object to be inspected is performed by observing an ultrasonic image formed by imaging processing, it is difficult to inspect the states of the welded portion and the weld defect, objectively and quantitatively with high accuracy.

2. It has been difficult to automatically determine whether an abnormality has been present or not, quantitatively and accurately, from information representing the states of the welded portion and the weld defect displayed in the ultrasonic image obtained by performing imaging processing on the inside of the object to be inspected.

Moreover, in a more specific example, in the known ultrasonic inspection apparatus, as a sensing device for ultrasonic inspection (ultrasonic sensor), an ultrasonic transducer including piezoelectric elements disposed in a matrix or an array for emitting and receiving an ultrasonic wave is used, and the ultrasonic wave is made incident on the object to be inspected by fastening and fixing a shoe material, which is an acoustic wave propagating liquid medium, to the emitting and receiving surfaces of the ultrasonic sensor with bolts and by bringing the shoe material into close contact with the object to be inspected.

A portion of the ultrasonic wave entering the object to be inspected, is reflected by internal defects and interfaces of the object to be inspected to be the reflection echo, and three-dimensional imaging of the inside of the object to be inspected is performed by receiving the reflection echo by means of the ultrasonic sensor, vibrating each piezoelectric element of the ultrasonic sensor, and processing the generated electric signals.

Moreover, since the ultrasonic wave can not propagate when an air layer is present between the ultrasonic sensor and the object to be inspected, a couplant for acoustic matching of the ultrasonic wave, is applied or interposed between the ultrasonic sensor and the shoe material and between the shoe material and the object to be inspected. As the couplant, a gel liquid or solid having low volatility is used. Air bubbles tends to exist in the portion in which the couplant is applied or interposed due to a temperature difference etc., thereby, before inspection of the object is performed by the ultrasonic inspection apparatus, it is required to confirm whether air bubbles are present or not. When air bubbles are found, the shoe material is removed and the couplant is again applied on the shoe material.

In such an ultrasonic inspection apparatus, air bubbles have tended to enter between the ultrasonic sensor and the shoe material, thus, each time entry of air bubbles have occurred, it has been required to remove from the shoe material from the ultrasonic sensor by removing the bolts, and to re-apply the couplant on the shoe material.

Moreover, when unevenness has been present on the surface of the object to be inspected, it is difficult to bring the shoe material into close contact with the object to be inspected by filling the gap using only the couplant.

In the ultrasonic inspection apparatus, when air bubbles have been present between the ultrasonic sensor and the object to be inspected, and therefore a gap have existed between them, since, it is difficult for the ultrasonic wave emitted from the ultrasonic sensor to enter the object to be inspected smoothly, and to receive the reflection echo, the ultrasonic wave and the reflection echo are not correctly propagated, resulting in problems that detection performance degraded, and three-dimensional imaging processing of the inside of the object to be inspected cannot be performed correctly and smoothly.

DISCLOSURE OF INVENTION

The present invention is performed in view of the above-mentioned considerations, and the object of the present invention is to provide a three-dimensional ultrasonic inspection apparatus that enables to perform three-dimensional internal inspection of the object to be inspected accurately and correctly in a non-destructive manner, quantitatively and automatically determine whether an abnormality is present or not by means of internal inspection.

Another object of the present invention is to provide a three-dimensional ultrasonic inspection apparatus that enables to obtain the size and position of the molten-solidified portion, solid-phase (corona bond), and the weld defect of the joined area rapidly as a high resolution ultrasonic test image by detecting the reflected echo of the ultrasonic wave emitted by each piezoelectric vibrator disposed in a matrix or an array, from the object to be inspected, and subjecting them to signal processing.

A further object of the present invention is to provide a three-dimensional ultrasonic inspection apparatus that enables to perform quantitative and stable determination of acceptability rapidly by verifying a database that stores pattern images of acceptability determination based on the ultrasonic test image in a suitable molten state with respect to an inspected ultrasonic test image.

A still further object of the present invention is to provide a sensing device for ultrasonic inspection that enables to improve detection performance by propagating an ultrasonic wave and the reflected echo correctly and smoothly, and three-dimensional imaging processing of the inside of an object to be inspected correctively, accurately, and effectively, and to provide a three-dimensional ultrasonic inspection apparatus including such a sensing device for ultrasonic inspection.

A still further object of the present invention is to provide a sensing device for ultrasonic inspection that allows shoe means to be attachable and detachable to and from a ultrasonic sensor simply and easily, and enables to shorten operation time, and to perform a ultrasonic test rapidly and effectively, and to provide a three-dimensional ultrasonic inspection apparatus including such a sensing device for ultrasonic inspection.

The above mentioned objects can be achieved according to the present invention by providing, in one aspect, a three-dimensional ultrasonic inspection apparatus comprising:

a sensing device for ultrasonic inspection including a transducer as an ultrasonic sensor having a plurality of piezoelectric vibrators disposed in a matrix or an array;

a drive element selecting unit for sequentially selecting piezoelectric vibrators from the plurality of piezoelectric vibrators constituting the ultrasonic transducer to produce an ultrasonic wave;

a signal detecting circuit for causing the ultrasonic wave produced by the piezoelectric vibrator selected by the drive element selecting unit to propagate through an acoustic wave propagating medium and enter a joined area of an object to be inspected for receiving a reflected echo from the joined area, and for detecting an electric signal corresponding to the reflected echo from the joined area;

a signal processing unit for subjecting the electric signal detected by the signal detecting circuit to signal processing, and generating three-dimensional imaging data by causing the electric signal to correspond to a mesh element partitioned in a three-dimensional imaging region set inside the object to be inspected; and a display processing device for displaying the detection results and three-dimensional image data from the signal processing unit, while detecting a size and a position of a molten-solidified portion, and a size and a position of a weld defect of the joined area from intensity distribution of the three-dimensional imaging data generated by the signal processing unit.

In this aspect, the display processing device may include:

a bottom portion data processing unit for detecting the size of a molten-solidified portion from strength distribution of three-dimensional imaging data of a bottom of the joined area of the object to be inspected generated by the signal processing unit;

an intermediate portion data processing unit for detecting presence or absence and the size of a molten defect of the joined area from the strength distribution of the three-dimensional imaging data of an intermediate joined area of the object to be inspected;

a determination unit for determining the acceptability of the object to be inspected by comparing detected results obtained by the bottom portion data processing unit with detected results obtained by the intermediate portion data processing unit; and a display unit for displaying the results obtained by the bottom portion data processing unit, the intermediate portion data processing unit and the determination unit, and displaying the three-dimensional imaging data generated by the signal processing unit.

Furthermore, in preferred embodiments of this aspect, the intermediate portion data processing unit of the display processing device may include:

an intermediate detection unit for generating a transmitting plane image of an intermediate joined surface by extracting three-dimensional imaging data of the intermediate portion of the joined area of the object to be inspected from the three-dimensional imaging data generated by the signal processing unit and for measuring the plate thickness; and a center position/joined area measuring unit for measuring the center position of the intermediate joined area, the size and the position of the joined area, and the size and the position of the weld defect such as a blowhole.

The bottom portion data processing unit of the display processing device may include:

a bottom detecting unit for generating a transmitting plane image by extracting three-dimensional imaging data of the bottom of the object to be inspected from the three-dimensional imaging data generated by the signal processing unit; and a molten-solidified portion detecting unit for measuring the size and the position of the molten-solidified portion from the transmitting plane image generated by the bottom detecting unit and the center position determined by the center position/joined area measuring unit.

The display processing device may include:

a determination unit for performing acceptability determination by comparing an acceptance standard obtained from a plate thickness of the object to be inspected obtained by the intermediate detection portion of the intermediate portion data processing unit, with the size and the position of the molten-solidified portion obtained by the molten-solidified portion detecting unit of the bottom data processing unit; and a display unit for displaying determination results in which a state of the joined area obtained by a center position/joined area determining unit of the bottom data processing unit and the state of the molten-solidified portion obtained by the determination unit are compared and displaying three-dimensional imaging data generated at the signal processing unit.

The intermediate data processing unit of the display processing device may include an intermediate detection unit including:

a surface/intermediate position detecting unit for detecting the surface position and the joined area position from three-dimensional imaging data generated by the signal processing unit;

a plate thickness measuring unit for measuring a plate thickness from data of a surface position and the joined area position generated by the surface/intermediate position detecting unit; and an intermediate position plane surface image generating unit for generating a transmitting plane surface image of the intermediate position from the intermediate position data obtained by the surface/intermediate position detecting unit and the three-dimensional imaging data generated by the signal processing unit.

The intermediate portion data processing unit of the display processing device may include a center position/joined area measuring unit, the center position/joined area measuring unit including:

a joined area contour determining unit for determining contours of the joined area from the intermediate position transmitting plane image generated by the intermediate detection unit;

a center position determining unit for determining the center position of the joined area from the contour data of the joined area obtained by the joined area contour determining unit; and a joined area measuring unit for measuring the size of the joined area from the contour data of the joined area obtained by the joined area contour determining unit.

The bottom portion data processing unit of the display processing device may include a bottom detecting unit, the bottom detecting unit including:

a dent portion/bottom position detecting unit for detecting a concave position representing a dent unit of the joined area and the bottom position of the object to be inspected from the three-dimensional imaging data generated by the signal processing unit;

a joined area thickness measuring unit for measuring the thickness of the joined area from the data of the concave portion/bottom position obtained by the dent portion/bottom position detecting unit; and a bottom position plane image generating unit for generating bottom position transmitting plane image from the data of concave portion/bottom position obtained by the dent portion/bottom position detecting unit and the three-dimensional imaging data generated by the signal processing unit.

The bottom portion data processing unit of the display processing device may include a molten-solidified portion detecting unit, the molten-solidified portion detecting unit including:

a strength distribution generating unit for generating a ultrasonic wave intensity distribution image from the bottom position transmitting plane image generated by the bottom detecting unit of the center position of the joined area obtained by a center position/joined area measuring unit of the intermediate portion data processing unit;

a smoothing processing unit for subjecting the ultrasonic wave intensity distribution image generated by the strength distribution generating unit to smoothing processing;

a primary differencing processing unit for subjecting the smoothed bottom position transmitting plane image to primary differencing in the direction from an outside to a center position;

a secondary differencing processing unit for subjecting the bottom position transmitting plane image subjected to primary differencing in the primary differencing processing unit to secondary differencing in the direction from an outside of the molten-solidified portion to a center position;

a molten-solidified portion identifying unit for identifying the molten-solidified portion of the joined area from inflection point data of the bottom position transmitting plane image subjected to secondary differencing; and a molten-solidified portion measuring unit for measuring the size of the molten-solidified portion from the molten-solidified portion data identified by the molten-solidified portion identifying unit.

The display processing device may include a determination unit for determining the acceptability of the joined state of the joined area, the determination unit including:

an acceptance standard generating unit for calculating a required size of the molten-solidified portion from a plate thickness "t" measured by the center position/joined area measuring unit of the intermediate portion data processing unit; and an acceptability determining unit for comparing a required size of the molten-solidified portion generated by an acceptance standard generating unit with the size of the molten-solidified portion measured by the molten-solidified portion detecting unit of the bottom portion data processing unit, and determining the acceptability of the joined state of the joined area.

The sensing device for ultrasonic inspection may include:

an ultrasonic sensor as a transducer having a plurality of piezoelectric elements for emitting and receiving the ultrasonic wave arranged in a matrix or an array; and a shoe member for holding a liquid medium which is provided on the side of the sensing surface of the ultrasonic sensor, the shoe member including: a tubular attachment provided to be freely attachable and detachable to and from the ultrasonic sensor through screw connection; a holding cap for fastening a thin film covering a top end opening of the attachment together with the attachment; and an acoustic wave propagating liquid medium filling the tubular attachment, and the thin film having a configuration swelling out from an opening of the holding cap and having flexibility.

The acoustic wave propagating liquid medium may be water, and the thin film may have a thickness equal to or less than a quarter of the wavelength λ of the ultrasonic wave propagating through the thin film.

The sensing device for ultrasonic inspection may include:

an ultrasonic sensor as an a transducer having a plurality of piezoelectric elements for emitting and receiving the ultrasonic waves arranged in a matrix or in an array;

a flexible shoe member provided on a side of the sensing surface of the ultrasonic sensor; and a sensor position adjusting member for containing the flexible shoe member and holding the ultrasonic sensor so as to be advanced and retracted with respect to the object to be inspected.

The flexible shoe member may include a soft shoe member having an excellent ultrasonic wave propagating property such as silicon rubber, and the sensor position adjusting member includes a holding frame for holding the ultrasonic sensor and supporting/adjusting bolts connected to the holding frame through screw connection at least at three points near the ultrasonic sensor, and the position of the ultrasonic sensor is adjusted by rotating the supporting/adjusting bolts around a bolt shank-line.

The sensing device for ultrasonic inspection may include:

an ultrasonic sensor as a transducer having a plurality of piezoelectric elements for emitting and receiving the ultrasonic wave arranged in a matrix or an array;

a shoe member for holding a liquid medium provided on a side of a sensing surface of the ultrasonic sensor; and a sensor holder having a medium reservoir supplying an ultrasonic wave propagating liquid medium to the shoe member.

The shoe member for holding a liquid medium may include: a spongy or porous flexible shoe member; and an ultrasonic wave propagating liquid medium that is poured by freely falling from the liquid medium reservoir in the shoe member to be accumulated and held in the shoe member.

When equipped with an air vent valve on the top thereof, a reservoir may include a sleeve-like or skirt-like tank guide covering a peripheral side surface of the flexible shoe member.

The sensing device for ultrasonic inspection may include:

an ultrasonic sensor as a transducer with a plurality of piezoelectric elements for emitting and receiving the ultrasonic wave being arranged; and a water-tank-type shoe member provided on a side of a sensing surface of the ultrasonic sensor, the shoe member including a reservoir for the ultrasonic wave propagating liquid medium which is constituted by a tank holding the ultrasonic sensor at the top of the tank and the object to be inspected placed so as to cover the bottom opening of the tank in a fluid-tight manner.

The water-tank-type shoe member may include: a circulation-type liquid medium supplying member for circulating the ultrasonic wave propagating liquid medium in the tank; and an air vent valve for venting air from a side of the top the tank.

The sensing device for ultrasonic inspection may include:

an ultrasonic sensor as a transducer having a plurality of piezoelectric elements for emitting and receiving the ultrasonic wave which are arranged in a matrix or an array;

a shoe member provided on a side of a sensing surface of the ultrasonic sensor; and a one-touch-type attaching member for detachably attaching the ultrasonic sensor to the ultrasonic sensor by one touch, wherein the shoe member is brought into close contact with the ultrasonic sensor and held against the ultrasonic sensor by the one-touch-type attaching member.

In another aspect of the present invention, there is provided a sensing device for ultrasonic inspection comprising:

an ultrasonic sensor as a transducer having a plurality of piezoelectric elements for emitting and receiving the ultrasonic wave which are arranged in a matrix or an array, and a shoe member for holding a liquid medium provided on a side of a sensing surface of the ultrasonic sensor, wherein the shoe member includes: a tubular attachment provided so as to be freely attachable and detachable to and from the ultrasonic sensor through screw connection; a holding cap for fastening a thin film covering a top end opening of the attachment together with the attachment; and an acoustic wave propagating liquid medium that fills the tubular attachment, the thin film having a configuration swelling out from the opening of the holding cap and having flexibility.

In a further aspect of the present invention, there is provided a sensing device for ultrasonic inspection comprising:

an ultrasonic sensor as an a transducer having a plurality of piezoelectric elements for emitting and receiving the ultrasonic waves which are arranged in a matrix or in an array;

a flexible shoe member provided on a side of a sensing surface of the ultrasonic sensor; and a sensor position adjusting member for containing the flexible shoe member and for holding the ultrasonic sensor so as to be advanced and retracted with respect to the object to be inspected.

In a still further aspect of the present invention, there is provided a sensing device for ultrasonic inspection comprising:

an ultrasonic sensor having a plurality of piezoelectric elements for emitting and receiving an ultrasonic wave which are arranged in a matrix or an array;

a shoe member for holding a liquid medium provided on a side of a sensing surface of the ultrasonic sensor; and a sensor holder having a medium reservoir supplying an ultrasonic wave propagating liquid medium to the shoe member.

In a still further aspect of the present invention, there is provided a sensing device for ultrasonic inspection comprising:

an ultrasonic sensor as a transducer with a plurality of piezoelectric elements for emitting and receiving an ultrasonic wave being arranged; and a water-tank-type shoe member provided on a side of a sensing surface of the ultrasonic sensor, the shoe member including a reservoir for the ultrasonic wave propagating liquid medium is constituted by a tank holding the ultrasonic sensor at the top of the tank and the object to be inspected placed so as to cover a bottom opening of the tank in a fluid-tight manner.

In a still further aspect of the present invention, there is provided a sensing device for ultrasonic inspection comprising:

an ultrasonic sensor as a transducer, in which a plurality of piezoelectric elements for emitting and receiving an ultrasonic wave are arranged in a matrix or an array;

a shoe member provided on a side of a sensing surface of the ultrasonic sensor; and a one-touch-type attaching member detachably attached to the ultrasonic sensor by one touch, wherein the shoe means is brought into close contact with the ultrasonic sensor and held against the ultrasonic sensor by the one-touch-type attaching member.

According to the present invention of the aspects mentioned above, by using the three-dimensional inspection apparatus, it is possible to perform internal inspection of the joined area of the object to be inspected rapidly, accurately, and correctly, in non-destructive manner, and to perform automatic examination by inspecting the presence or absence of abnormality, which is the size and the position of the molten-solidified portion and the molten defect quantitatively and accurately through the internal inspection.

Moreover, since the ultrasonic transducer includes piezoelectric vibrator disposed in a matrix or array therein, it is possible to obtain the sizes and positions of the molten-solidified portion, solid-phase welded portion, and the weld defect of the joined area rapidly as high resolution ultrasonic diagnostic images by sequentially activating each piezoelectric vibrator to produce ultrasonic waves, then detecting the reflected echoes reflected by the joined area of the object to be inspected and subjecting them to signal processing.

Furthermore, by storing an acceptability determination pattern image using an ultrasonic flaw image in a suitable welded state as the standard, and comparing and referencing a detected ultrasonic flaw image of the object to be inspected to the stored ultrasonic flaw image of the standard, it is possible to perform a stable acceptability determination rapidly, automatically, and quantitatively.

In addition, since the sensing device for ultrasonic inspection can detect the reflected echoes correctly and effectively by emitting and receiving the ultrasonic waves smoothly from the an ultrasonic sensor as a transducer, in which a plurality of piezoelectric elements emitting and receiving ultrasonic waves are arranged by using the sensing device for ultrasonic inspection, detection performance and detection accuracy can be improved, and a high resolution and high accuracy three-dimensional imaging processing of the inside of the object can be performed by detecting the electric signals of the reflected echoes accurately, thus enabling to perform a correct, accurate and effective non-destructive ultrasonic inspection of the inside of the object to be inspected.

Still furthermore, since, by using the sensing device for ultrasonic inspection, the shoe member of the ultrasonic sensor as a transducer, in which a plurality of piezoelectric elements emitting and receiving ultrasonic waves are arranged, can be removed and attached simply and easily, while working hours being decreased, even if the object to be inspected has a curved surface, the ultrasonic sensor as a transducer can be correctly and smoothly brought into close contact with the object to be inspected, thus enabling to perform a rapid and accurate ultrasonic inspection.

BEST MODE FOR CARRYING OUT THE INVENTION

Hereinafter, embodiments of a three-dimensional ultrasonic inspection apparatus according to the present invention will be described with reference to the accompanying drawings.

Figure 1:
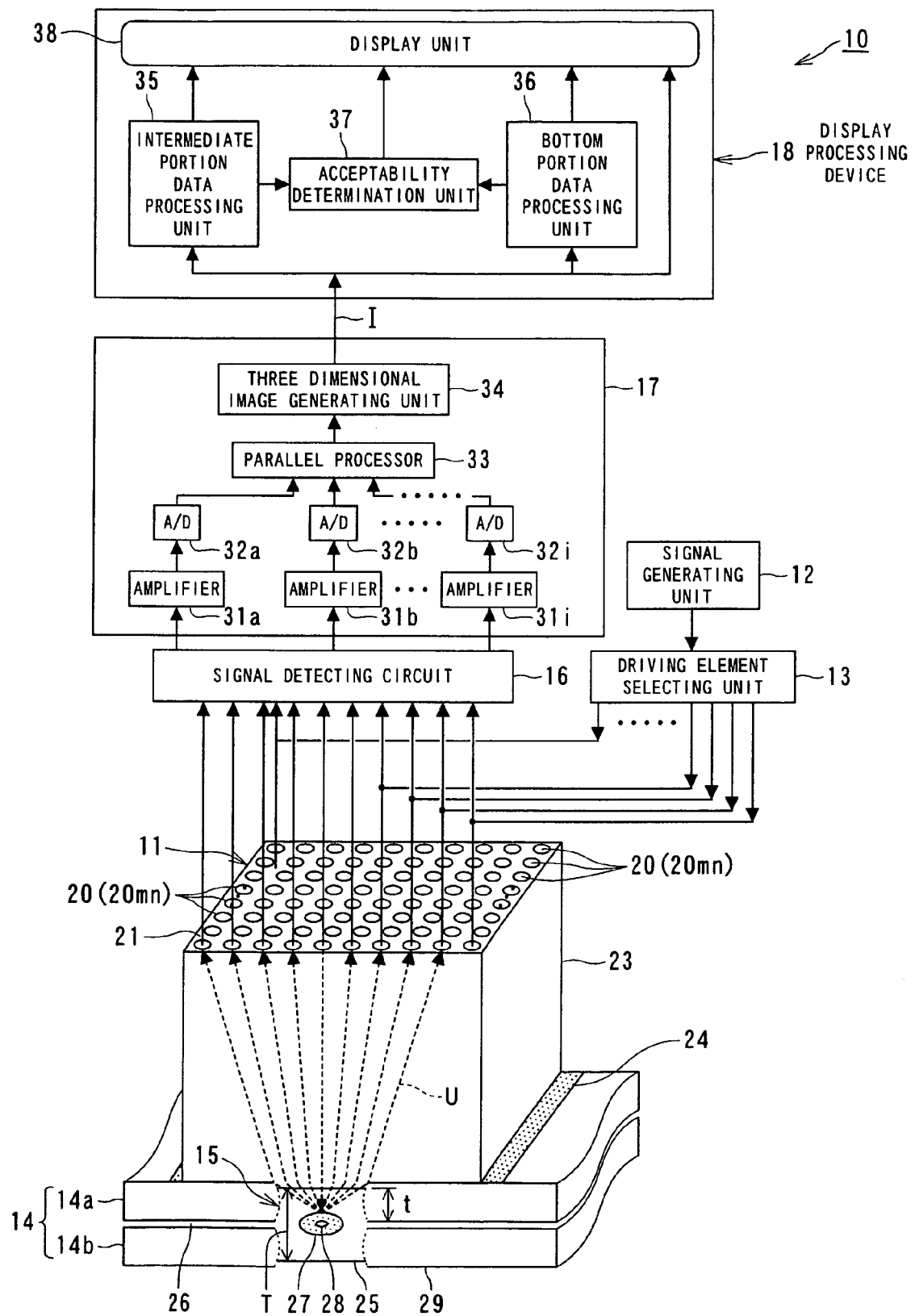
FIG. 1 is an entire configuration view showing one embodiment of a three-dimensional ultrasonic inspection apparatus according to the present invention.

FIG. 1 is a configuration view showing one embodiment of the three-dimensional ultrasonic inspection apparatus according to the present invention.

The three-dimensional ultrasonic inspection apparatus 10 includes: a sensing device 100 for ultrasonic inspection (details thereof will be described below) including a transducer 11 as an ultrasonic sensor that causes an ultrasonic vibration to be converted into an electric signal and vice versa, and emits and receives an ultrasonic wave having an required frequency; a signal generating unit 12 for generating a drive signal for driving the ultrasonic transducer 11; a driving element selecting unit 13 for selectively driving a piezoelectric vibrator of the ultrasonic transducer 11 by selecting a drive signal of the signal generating unit 12; a signal detecting circuit 16 for irradiating an ultrasonic wave produced by the ultrasonic transducer 11 to a welded area 15, which is the joined area of the object to be inspected 14, and then detecting the signal of a reflected echo from the welded area 15 via the ultrasonic transducer 11; a signal processing unit 17 for generating a three-dimensional (3D) ultrasonic image by subjecting an electric signal corresponding to the reflected echo detected by the signal detecting circuit 16 to parallel arithmetic processing; and a display processing device 18 for displaying a determination result by further subjecting the ultrasonic test image processed in the signal processing unit 17 to obtain a high-resolution three-dimensional ultrasonic test image and then by automatically and accurately determining the states of the internal structure and the joined area 15 and the state of the weld defect 16.

The ultrasonic transducer 11 has a configuration where a large number of piezoelectric vibrators 20 are aligned and arranged in a state of matrix having "m" rows and "n" columns so as to constitute a matrix sensor, which is the sensing device 100 for ultrasonic inspection.

A drive signal generated by the signal generating unit 12 is selected by the driving element selecting unit 13 and applied to the each piezoelectric vibrator 20mn of the ultrasonic transducer 11. The piezoelectric vibrators 20mn can be driven individually or in groups, by means of selection of the driving element selecting unit 13; at a required drive timing. Instead of being disposed in a matrix, each piezoelectric vibrator 20 may be arranged in a row or in a cross line so as to constitute an array sensor.

A liquid or solid acoustic wave propagating medium 23 is brought into close contact with the surface for emitting and receiving ultrasonic waves, which is a sensing surface of the ultrasonic transducer 11, specifically, the side of the object to be inspected 14. A couplant 24 for acoustic matching of the ultrasonic waves is provided between the acoustic wave propagating medium 23 and the object to be inspected 14. When a liquid such as water is used as the acoustic wave propagating medium 23, the couplant is not required.

Moreover, when the acoustic wave propagating medium 23 has a shape of a box, the area of an opening of which is formed in accordance with the size of the joined area 15, which is the inspecting region (target region) of the object to be inspected 14, the height of the acoustic wave propagating medium 23 is determined by the oscillation angle (spreading angle) of the ultrasonic wave produced by the piezoelectric vibrators 20.

As the object to be inspected 14, for example, two plate-like structures 14a and 14b joined by means of spot welding, are considered, and a spot welded area of the structures 14a and 14b is subjected to an internal inspection in a non-destructive manner by the three-dimensional ultrasonic inspection apparatus 10 using ultrasonic waves. As the object to be inspected 14, an object having three or more pieces of plate-like structures welded by superposing them may be used. The object to be inspected 14 may be a metallic material or a resin material.

When the two plate-like structures 14a and 14b are joined by being superposed and spot welded, a concave portion 25 as a dent portion is formed on the outer surface of the joined area of the plate-like structure 14 by a welding electrode. Thus, the thickness T of the joined area 15 becomes smaller than that of a non-joined area 26 around the joined area 15 by an amount of formation of the concave portion 25.

In FIG. 1, reference numeral 27 denotes molten-solidified portion of the joined area 15, and reference numeral 28 denotes a weld defect such as a blowhole that exists in the joined area 15.

Meanwhile, the signal generating unit 12 for supplying a drive signal to the ultrasonic transducer 11, in order to generate ultrasonic waves by actuating the piezoelectric substance of the piezoelectric vibrators 20, generates a pulsed or continuous drive signal. For the generated drive signal, the piezoelectric vibrators 20mn to be driven by the driving element selecting unit 13 are selected, and the drive signal is supplied to the selected piezoelectric vibrators 20mn at a required timing. Since the driving element selecting unit 13 sequentially selects one or a plurality of the piezoelectric vibrators 20 to be driven at the required timing, when the drive signal from the signal generating unit 12 is supplied to the selected piezoelectric vibrators 20, the piezoelectric vibrators 20 are driven so as to produce an ultrasonic wave U having a required frequency.

The ultrasonic waves sequentially produced by the piezoelectric vibrators 20mn of the ultrasonic transducer 11,-pass through the acoustic wave propagating medium 23, enter the object to be inspected 14 via the couplant 24, reach the inspecting regions 15 of the object to be inspected 14 (the non-joined area 26, the molten-solidified portion 27, the weld defect portion 28 such as a blowhole, and the bottom 29), and are reflected at boundary layers.

The echoes reflected from the boundary layers of the bottom 9, the non-joined area 26, the molten-solidified portion 27, the weld defect portion 28 such as a blowhole of the object to be inspected 14, is input from the object to be inspected 14 to the sensing device 100 for ultrasonic inspection via the acoustic wave propagating medium 23. In the sensing device 100 for ultrasonic inspection, each reflected echoes is input into piezoelectric vibrators 20 of the ultrasonic transducer 11 used as a matrix sensor, with a different time lag. The reflected echoes input into the piezoelectric vibrators 20 are converted into electric signals and input to the signal detecting circuit 16, where, the electric signals of the reflected echoes are each detected with respect to the corresponding piezoelectric vibrator 20.

In the three-dimensional ultrasonic inspection apparatus 10, when a drive signal is applied to the piezoelectric vibrators 20mn selected by the driving element selecting unit 13, among the piezoelectric vibrators 20 of the ultrasonic transducer 11, the piezoelectric vibrators 20mn operate to produce ultrasonic waves U. The ultrasonic waves U are irradiated to the inspecting region, which is the joined area 15 of the object to be inspected 14, via the acoustic wave propagating medium 23 and the couplant 24 if necessary. Portions of the ultrasonic waves U irradiated to the inspecting region 15 of the object to be inspected 14 are reflected from a density boundary layer of the inspecting region 15 and are reflected as echoes. The reflected echoes are received by the piezoelectric vibrators 20 of the matrix sensor (the ultrasonic transducer 11) with a different time lag via the couplant 24 and the acoustic wave propagating medium 23, send to the signal detecting circuit 16 as the electric signals corresponding to the reflected echoes obtained by means of piezoelectric transformation performed by the piezoelectric vibrators 20, and detected.

In the ultrasonic transducer 11, since the piezoelectric vibrators 20mn are sequentially driven at a required timing, by the drive signals which are sequentially supplied from the drive signal selecting unit 13, reflected echoes of the ultrasonic waves produced by the piezoelectric vibrators 20mn are received by the matrix sensor 11 in a two dimensional-manner. When "m" rows and "n" columns of the piezoelectric vibrators 20mn, for example, one hundred (10×10) piezoelectric vibrators 20mn are disposed in a matrix, if drive signals are sequentially supplied to the piezoelectric vibrators 20mn by the driving element selecting unit 13, the ultrasonic transducer 11 is configured so that the ultrasonic waves U are sequentially produced by the piezoelectric vibrators 20mn at a timing with which the drive signals are sequentially supplied to the piezoelectric vibrators 20mn, the reflected echoes of the ultrasonic waves sequentially produced by the piezoelectric vibrators 20mn are sequentially received by the matrix sensor 11, and the electric signals corresponding to the reflected echoes, which are the received signals, are send to the signal detecting circuit 16 every time the reflected echoes are received.

Consequently, in the signal detecting circuit 16, the reflected echoes of the ultrasonic waves, produced by the individual piezoelectric vibrators 20mn disposed in a matrix by means of operation of the ultrasonic transducer 11, are received by the matrix sensor 11 in a two-dimensional manner. The matrix sensor 11 receives reflected echoes corresponding to the ultrasonic waves produced by the individual piezoelectric vibrators 20mn, the electric signals corresponding to the received reflected echoes are sent to the signal detecting circuit 16, and sent to the signal processing unit 17 via the signal detecting circuit 16.

The signal detecting circuit 16 has a function of detecting the electric signals corresponding to the reflected echoes produced by the matrix sensor 11. Among the detected signals, a plurality of signals required for inspection are each supplied to one of amplifiers 31a, 31b, . . . , and 31i in the signal processing unit 17.

The amplifiers 31a, 31b, . . . , and 31i have a function of amplifying the supplied electric signals corresponding to the reflected echoes, and to supply the amplified electric signals to A/D converters 32a, 32b, . . . , and 32i, respectively. The A/D converters 32a, 32b, . . . , and 32i have functions of subjecting the supplied electric signals to A/D conversion, and of supplying the converted electric signals to parallel processors 33a, 33b, . . . , and 33i, respectively.

The parallel processors 33 in the signal processing unit 17 have functions of subjecting the digital signals supplied from the A/D converters 32a, 32b, . . . , and 32i, to rapid arithmetic processing in parallel, and of identifying the reflected intensity from mesh elements divided into inspecting regions (imaging regions). The identified reflected intensity are unified by a three-dimensional image generating unit 34 into three-dimensional imaging information (data), and sent to the display processing device 18. The display processing device 18 has a function of, while subjecting the supplied three-dimensional imaging data to data processing in an intermediate portion data processing unit 35 and a bottom portion data processing unit 36, determining the acceptability of the inspecting region (measuring area) 15 of the object to be inspected 14 in a determination unit 37, and displaying the determined acceptability result and the three-dimensional ultrasonic image supplied by the three-dimensional image generating unit 34 on the displaying unit 38 as an ultrasonic test image.

Figure 2:
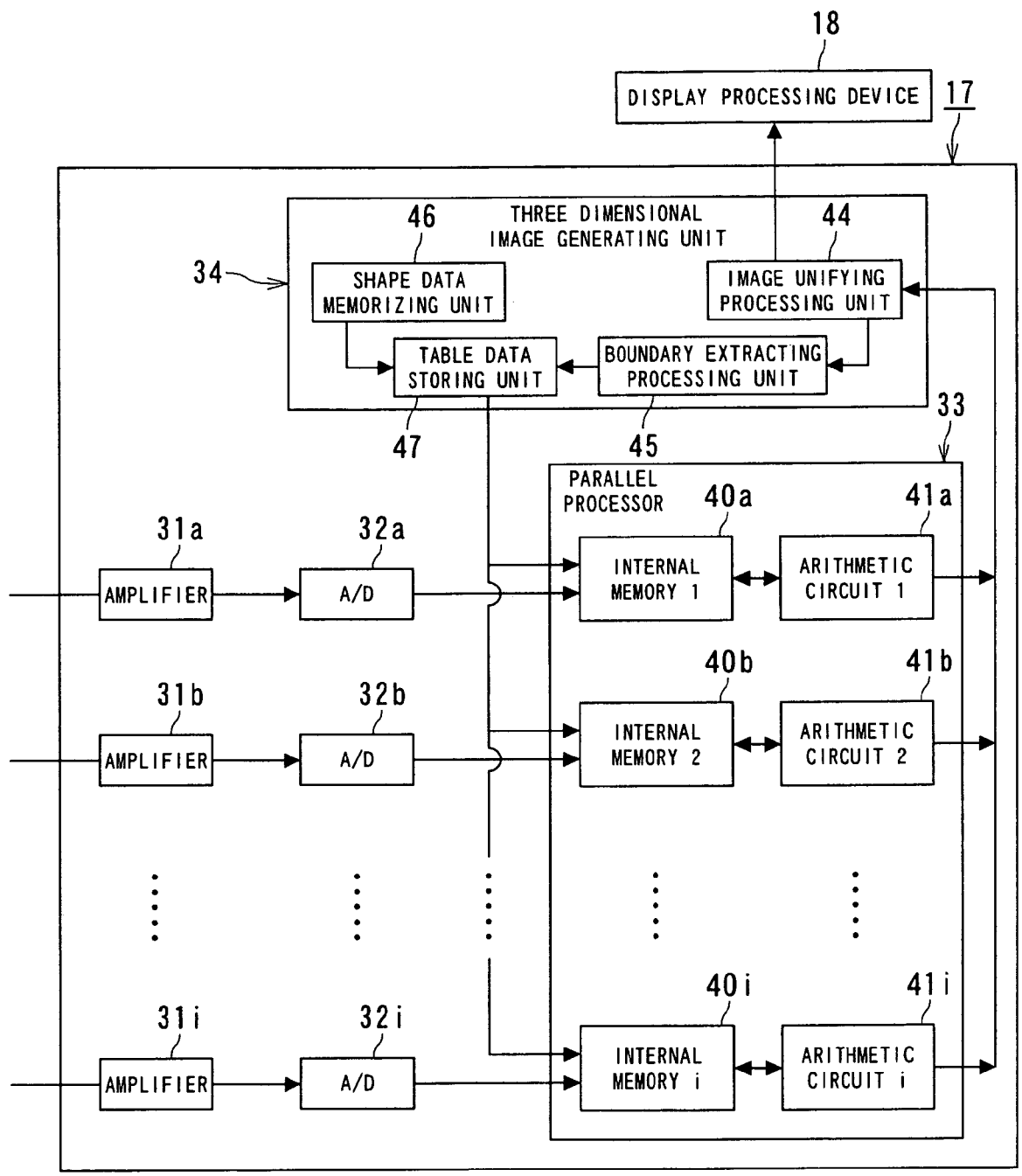
FIG. 2 is a block diagram showing the configuration of a signal processing unit equipped to the three-dimensional ultrasonic inspection apparatus according to the present invention.

The signal processing unit 17 of the three-dimensional ultrasonic inspection apparatus 10 shown in FIG. 1 mentioned above, is configured as shown in FIG. 2.

The parallel processors 33 included in the signal processing unit 17 have inner memories 40a, 40b, . . . , and 40i and arithmetic circuits 41a, 41b, . . . , and 41i, respectively. The three-dimensional image generating unit 34, which is an unified processor, has an image unifying processing unit 44, a boundary extracting processing unit 45, a shape data memorizing unit 46, and a table data storing unit 47.

The inner memories 40a, 40b, . . . , and 40i have functions of temporarily storing the A/D converted signals supplied from the A/D converters 32a, 32b, . . . , and 32i, and propagation time data obtained by the table data storing unit 47, respectively. The arithmetic circuits 41a, 41b, . . . , and 41i have functions of identifying the reflection intensities from the mesh elements of the imaging region (inspecting region) and to cause each mesh element to correspond to a reflection intensity. The reflection intensities corresponding to the mesh elements are supplied to an image unifying processing unit 44 of the three-dimensional image generating unit (unifying processor) 34.

The image unifying processing unit 44 has a function of generating three-dimensional imaging data by adding the supplied reflection intensities with respect to each mesh element of the inspecting region. The generated three-dimensional (3D) imaging data is supplied to the display processing device 18.

Meanwhile, the boundary extracting processing unit 45 has a function of extracting a boundary existing inside the object to be inspected 14 from the result output from the image unifying processing unit 44. Information regarding the extracted boundary is sent to the table data storing unit 47.

The shape data memorizing unit 46 has a function of memorizing the information regarding to the surface shape and the boundary layer structure with respect to the object to be inspected 14, in advance. The memorized information is sent to the table data storing unit 47, if required.

The table data storing unit 47 has a function of storing ultrasonic wave propagating times (or equivalent distances may be used) between each of the piezoelectric vibrators 20mn of the matrix sensor 11 in advance by tabling the ultrasonic wave propagating times. A portion or the whole of the stored ultrasonic wave propagating times is transferred to the inner memories 40a, 40b, . . . , and 40i of the parallel processors 33, if required.

Moreover, the ultrasonic wave propagating times stored in the table data storing unit 47 can be reset using the information regarding the extracted boundary in the object to be inspected 14 supplied by the boundary extracting processing unit 45, and the information regarding the surface shape or layer structure with respect to the object to be inspected 14.

In such a manner, the parallel processors 33 and the three-dimensional (3D) image generating unit 34 in the signal processing unit 17 have a function of generating three-dimensional imaging data I for visualizing the state of the joined area 15 by processing the digital signals supplied from the A/D converters 32a, 32b, . . . , and 32i. The three-dimensional imaging data is generated by causing the electric signals corresponding to the reflected echoes, detected by the signal detecting circuit 46, to each correspond to one of the mesh elements of the three-dimensional imaging region set inside the object to be inspected 14 by means of opening-synthesizing processing.

The three-dimensional image generating unit 34 generates three plane (two-dimensional) images by seeing through the three-dimensional imaging data I from three directions, which are a front (X-Y plane) direction viewed from the ultrasonic transducer 11 and two directions (Y-Z plane) and (Z-X plane) perpendicular to the front direction and each other, and projecting the largest data value of the imaging data, superposed in the see-through directions of the three-dimensional imaging data I, in the three directions on a plane. The three-dimensional imaging data I generated by the three-dimensional image generating unit 34 is output to the display processing device 18.

The intermediate portion data processing unit 35 of the display processing device 18 detects the state of the joined area 15 by extracting a transmitting front surface image of the intermediate layer region near the joined area 15 of the two plate-like structures 14a and 14b from the intensity distribution of the three-dimensional imaging data I. The bottom portion data processing unit 36 extracts the size of the molten-solidified portion 27 by extracting the transmitting front image of the bottom portion 29 from the intensity distribution of the three-dimensional imaging data I. Furthermore, the determination unit 37 compares the results obtained by the intermediate portion data processing unit 35 and the bottom portion data processing unit 36 and performs determination. The display unit 38 displays respective comparison and determination results obtained by the intermediate portion data processing unit 35, the bottom portion data processing unit 36, and the determination unit 37, and the three-dimensional imaging data I from the three-dimensional image generating unit 34.

Next, with reference to FIG. 3, the function of the display processing device 18 of the three-dimensional ultrasonic inspection apparatus 10 will be described.

The intermediate portion data processing unit 35 of the display processing device 18 includes an intermediate detection unit 50 and a center position/joined area measuring unit 51. The intermediate detection unit 50 extracts three-dimensional imaging data of the intermediate joined area 15 from the three-dimensional imaging data I generated by the signal processing unit 17, generates a transmitting plane image of the intermediate joined surface, and measures the plate thickness "t" of the plate-like structure 14a. Moreover, from the transmitting plane image of the intermediate joined area generated by the intermediate detection unit 50, the center position/joined area measuring unit 51 measures the center position of the intermediate joined area, the size and the position of the joined area 15, and the size and the position of the weld defect such as a blowhole.

Meanwhile, the bottom portion data processing unit 36 of the display processing device 18 includes a bottom detecting unit 53 and the molten-solidified portion detecting unit 54. The bottom detecting unit 53 generates a transmitting plane image of the bottom 29 of the object to be inspected 14 from the three-dimensional imaging data I generated by the signal processing unit 17, and measures the thickness T of the joined area 15. Moreover, the molten-solidified portion detecting unit 54 measures the size and the position of the molten-solidified unit 27 from the transmitting plane image of the bottom 29, generated by the bottom detecting unit 53, and the center position of the intermediate joined area 15 taken from the center position/joined area measuring unit 51.

Moreover, the determination unit 37 of the display processing device 18 performs acceptability determination by calculating the minimum required size of the molten-solidified unit 27 from the plate thickness "t" of the plate-like structure 14a, incorporated from the intermediate detection unit 50, setting the calculated acceptance standard of the size of the molten-solidified unit 27, and comparing the size and the position of the molten-solidified unit 27 taken from the molten-solidified portion detecting unit 54 to those of the set acceptance standard values. The determination standard can be defined by a pattern image of acceptability determination stored in the database based on an ultrasonic test image of a suitable state. The pattern image of acceptability determination is memorized in the database of the determination unit 37 in advance, and stored.

The display unit 38 displays the transmitting plane image of the intermediate joined surface used in the center position/joined area measuring unit 51, the center position of the intermediate joined area and the size and the position of the joined area 15 measured from the transmitting plane image, the size and the position of the weld defect unit 28 such as a blowhole, the transmitting plane image of the bottom used in the molten-solidified portion detecting unit 54, and the measured size and position of the molten-solidified unit and the acceptance standard value and the acceptability determination.

Figure 4:
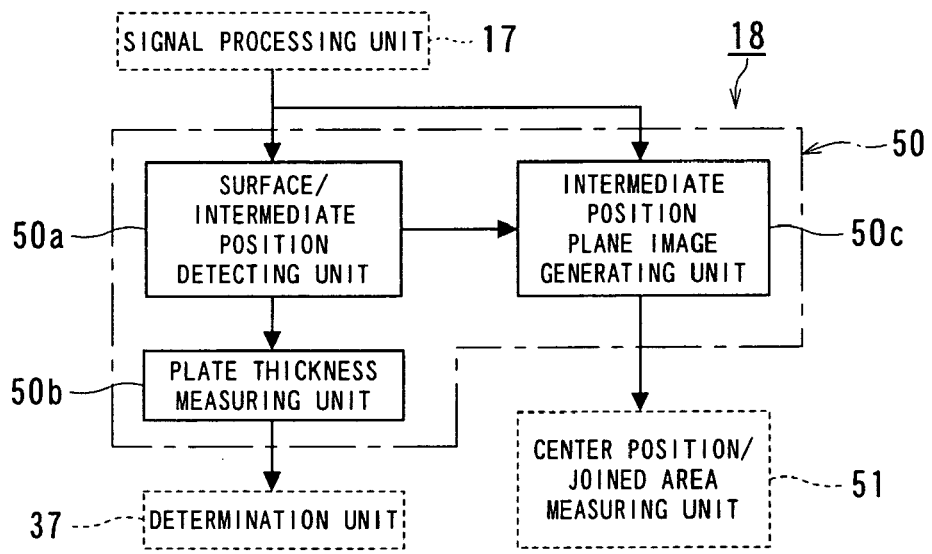
FIG. 4 is a block diagram explaining the data processing of an intermediate detection unit in the display processing device shown in FIG. 3.

FIG. 4 is a view explaining the function of the intermediate detection unit 50 of the display processing device 18 of the three-dimensional ultrasonic inspection apparatus 10.

The intermediate detection unit 50 of the display processing device 18 has a surface/intermediate position detecting unit 50c for detecting the surface and the intermediate position of the object to be inspected, a plate thickness measuring unit 50b for measuring the plate thickness "t" of the plate-like structure 14a, and an intermediate position plane image generating unit 50c for forming the plane image of the intermediate layer region.

The imaging data of the sides perpendicular to the front, among the three-dimensional imaging data I generated by the signal processing unit 17, includes information in the thickness direction on the plurality of plate-like objects to be inspected having the joined area 15. The surface/intermediate position detecting unit 50a determines the bottom of the plate-like structure (flat plate) 14a, which is the intermediate layer position (thickness direction) of the joined area 15 by using the fact that, in the non-joined area where the plate-like objects are not joined, the reflection intensity from the bottom of the first flat plate viewed from the matrix sensor 11 is high.

The plate thickness measuring unit 50b measures the thickness "t", of the first flat plate from the bottom position (thickness direction) of the first flat plate determined in the surface/intermediate position detecting unit 50a.

The surface/intermediate position detecting unit 50c of the intermediate detection unit 50 extracts imaging data in the front direction of the intermediate layer area only, from the three-dimensional imaging data I generated in the signal processing unit 17. Since, in the intermediate layer area, the non-joined area 26 having a high reflection intensity and the joined area 15 having a low reflection intensity are present, the boundary between the non-joined area 26 and the joined area 15 clearly appears as the shape of a joined area contour. Moreover, the weld defect unit 28 such as a blowhole generated in the molten-solidified portion 27 inside the joined area 15 also appears in the imaging data in the front direction of the intermediate layer portion.

Figure 5:
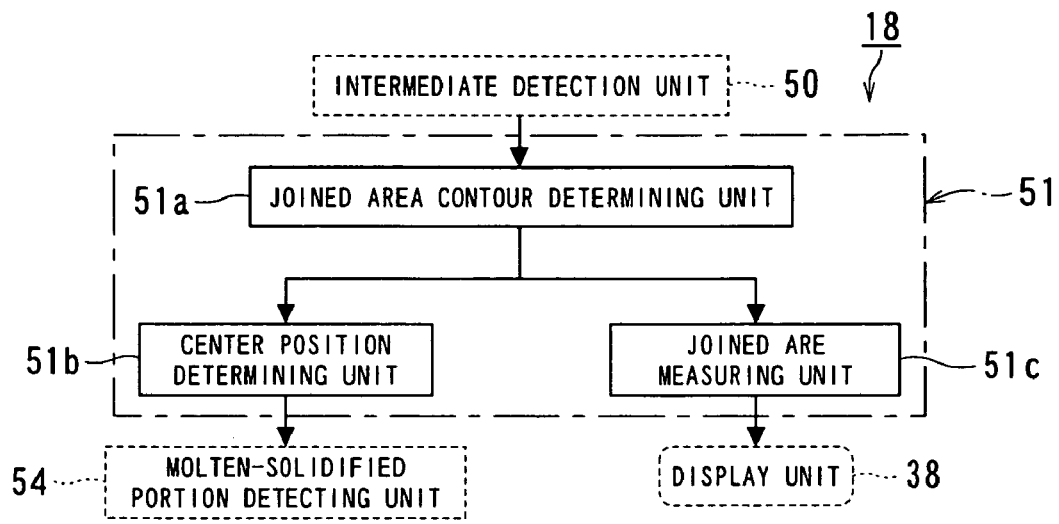
FIG. 5 is a block diagram explaining the data processing of a center position/joined area measuring unit in the display processing device shown in FIG. 3.

FIG. 5 is a view explaining the function of the center position/joined area measuring unit 51 of the display processing device 18 of the three-dimensional ultrasonic inspection apparatus 10.

The joined area contour determining unit 51a recognizes the size and the position of the shape of the joined area contour which appears in the imaging data in the front direction of the intermediate layer only, extracted in the intermediate detection unit 50, as the difference between reflection intensities, as imaging data. At the same time, the shape, the size, and the position of the blowhole 28 generated in the molten-solidified unit 27 inside the joined area 15, are also recognized as imaging data.

The center position determining unit 51b calculates the center position of the joined area 15 from the contour data of the joined area 15 recognized by the joined area contour determining unit 51a.

The joined area measuring unit 51c measures the size and the position of the shape of the joined area contour from the contour data of the joined area 15 recognized by the joined area contour determining unit 51a. In addition, since there is difference in reflection intensity between the molten-solidified portion 27 inside the joined area 15 and the weld defect portion 28 such as a blowhole, the molten-solidified portion 27 and the weld defect portion 28 are distinguished using the difference.

Figure 6:
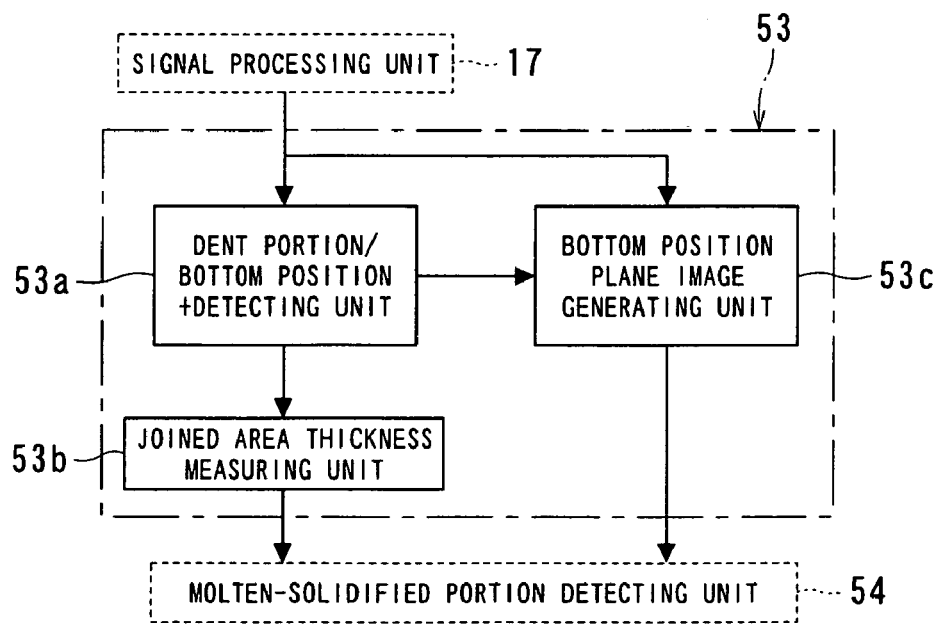
FIG. 6 is a block diagram explaining the data processing of a bottom detecting unit in the display processing device shown in FIG. 3.

FIG. 6 is a view explaining the function of the bottom detecting unit 53 of the display processing device 18 of the three-dimensional ultrasonic inspection apparatus 10.

The bottom detecting unit 53 of the surface display device 18 has a dent portion/bottom position detecting unit 53a for detecting the concave portion (dent portion) and the bottom 29 of the object to be inspected 14, a joined area thickness measuring unit 53b for detecting the thickness "T" of the joined area 15, and a bottom position plane image generating unit 53c.

The imaging data at the sides perpendicular to the front, among the three-dimensional imaging data I generated by the signal processing unit 17, includes the information in the thickness direction of the plurality of plate-like objects to be inspected 14 having the joined areas 15. The dent portion/bottom position detecting unit 53a determines the bottom position of the whole of the plurality of plate-like objects to be inspected 14 from the reflection position at the thickest portion.

The joined area thickness measuring unit 53b measures the thickness "T" of the objects to be inspected 14 from the bottom position (thickness direction) of the objects to be inspected 14 determined in the dent portion/bottom position detecting unit 53a.

The bottom position plane image generating unit 53c generates the imaging data in the front direction of the bottom area only from the three-dimensional imaging data I generated in the signal processing unit 17. The bottom area imaging data includes the information on the weld defect area 28 such as the molten-solidified portion 27 inside the joined area 15. The blowhole inside the molten-solidified portion 27, however, without any action, and although the joined area 15 and the blowhole can be distinguished from the difference between their reflection intensities, the joined area 15 and the molten-solidified portion 27 can not be distinguished due to the small difference between their reflection intensities.

Figure 7:
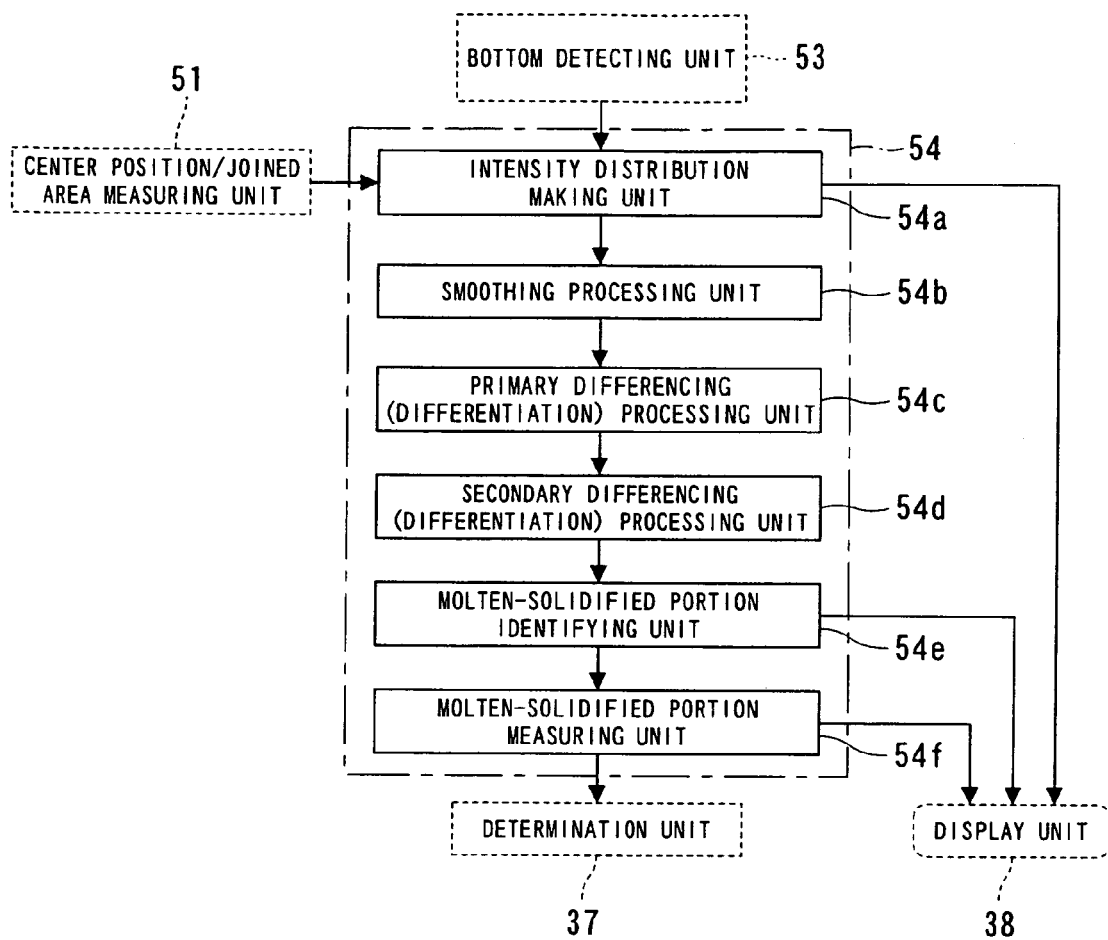
FIG. 7 is a block diagram explaining the data processing of a melt coagulation area detecting unit in the display processing device shown in FIG. 3.

FIG. 7 is a view explaining the function of the molten-solidified portion detecting unit 54 of the display processing device 18 of the three-dimensional ultrasonic inspection apparatus 10.

The molten-solidified portion detecting unit 54 of the display processing device 18 includes: a strength distribution generating unit 54a for generating the ultrasonic wave intensity distribution image of the bottom position of the object to be inspected 14; a smoothing processing unit 54b for subjecting the ultrasonic wave intensity distribution image data to smoothing processing, a primary differencing (primary differentiating) processing unit 54c for subjecting the bottom position transmitting plane image of the joined area 15 subjected to the smoothing processing to (primary) differencing processing; a secondary differencing (secondary differentiating) processing unit 54d for subjecting the bottom position transmitting plane image of the joined area 15 subjected to the differencing processing to differencing processing (a secondary differencing processing, or a secondary differentiating processing); a molten-solidified portion specifying unit 54e for specifying the molten-solidified portion 27 of the joined area 15; a molten-solidified portion specifying unit 54e for specifying the molten-solidified portion 27 for measuring the size and the position of the molten-solidified portion 27; and a molten-solidified portion measuring unit 54f for measuring the size and the position of the molten-solidified portion 27.

The strength distribution generating unit 54a of the molten-solidified portion detecting unit 54 generates the ultrasonic wave intensity distribution image of the bottom position including the center position information of the joined area 15 from the bottom position transmitting plane image generated by the bottom detecting unit 53 and the center position of the joined area 15 taken from the center position/joined area measuring unit 51.

The smoothing processing unit 54b of the molten-solidified portion detecting unit 54 subjects the ultrasonic wave intensity distribution image data to the smoothing processing in order to remove noise included in the ultrasonic wave intensity distribution image data generated by the strength distribution generating unit 54a.

The bottom area imaging data subjected to the smoothing processing by the smoothing processing part unit 54b includes the information on the weld defect area 28 such as the molten-solidified portion 27 inside the joined area 15 and the blowhole inside the molten-solidified portion 27. Although, without any measure, the boundary between the joined area 15 and the blowhole area 28 can be determined from the difference between their reflection intensities, the boundary between the joined area 15 and the molten-solidified portion 27 cannot be determined due to the small difference between their reflection intensities.

Figure 8:
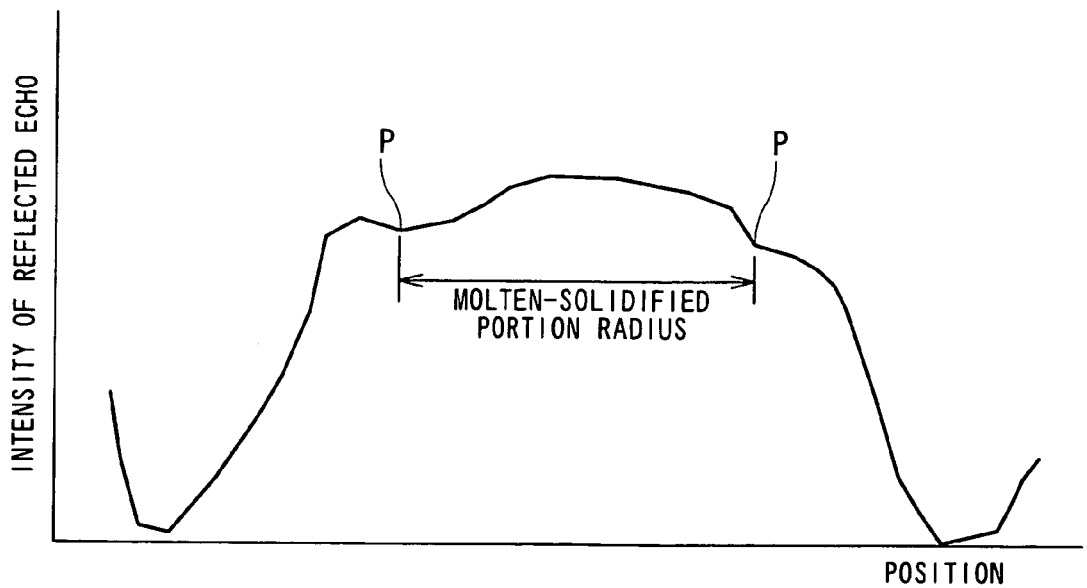
FIG. 8 is a view explaining the concept of a molten-solidified portion detection of the region to be inspected, which is the joined area of an object to be inspected.

However, as shown in FIG. 8, the boundary between the joined area 15 and the molten-solidified portion 27 inside the joined area appears as an inflection point P of the reflection echo intensity of the bottom position transmitting plane image subjected to smoothing processing in the smoothing processing unit 54b viewed in the direction from the outside of the joined area 15 to the center position. Consequently, when subjecting the bottom position transmitting plane image of the joined area 15 subjected to the smoothing processing in the smoothing processing unit 54b to the primary differencing (primary differentiating) processing in the direction from the outside to the center position in the primary differencing (primary differentiating) processing unit 54c, and further subjecting the bottom position transmitting plane image of the joined area 15 to the secondary differencing (secondary differentiating) processing similarly in the secondary differencing (secondary differentiating) processing unit 54d, the imaging data of the inflection point P of the bottom position transmitting plane image can be obtained.

The molten-solidified portion specifying unit 54e specifies the molten-solidified portion 27, which is an area termed a nugget in spot welding, from the imaging data of the inflection point P of the bottom position transmitting plane image obtained in the secondary differencing (secondary differentiating) processing unit 54d. Although, the imaging data of the inflection point P would be a continuous curve showing the contour of the molten-solidified portion 27, in practice, sometimes only non-continuous curve data is obtained. When only the non-continuous curve data is obtained, using the center position data of the joined area 15 taken from the center position/joined area measuring unit 51 in the strength distribution generating unit 54a, the continuous curve showing the contour of the molten-solidified portion 27 can be obtained from the non-continuous curve data and the center position data by means of calculation.

The molten-solidified portion measuring unit 54f recognizes the shape size and the position of the molten-solidified portion 27 from the contour data of the molten-solidified portion 27 obtained by the molten-solidified portion specifying unit 54e, as image data. The solid phase joined area (nugget) of a heat-affected layer formed on the outer periphery of the molten-solidified portion 27 can be obtained by an arithmetic processing by analyzing the joined area 15 and the molten-solidified portion 27.

Figure 9:
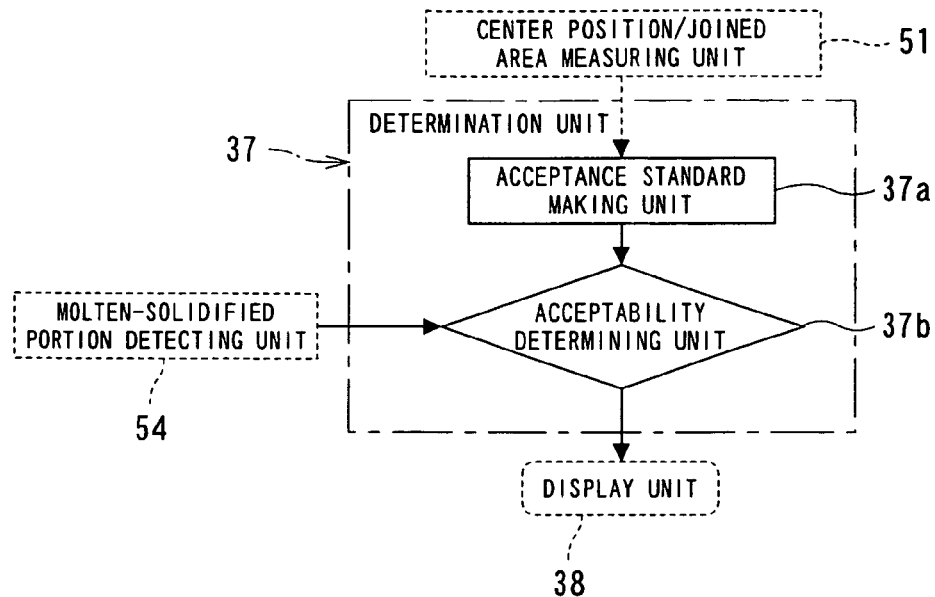
FIG. 9 is a block diagram explaining the data processing of an acceptability determinating unit in the display processing device shown in FIG. 3.

FIG. 9 is a view explaining the function of the determination unit 37 of the display processing device 18 of the three-dimensional ultrasonic inspection apparatus 10.

The determination unit 37 of the display processing device 18 includes an acceptance standard generating unit 37a and an acceptability determining unit 37b.

The acceptance standard generating unit 37a of the determination unit 37 calculates the minimum required size of the molten-solidified portion 27 from the plate thickness "t" obtained by the center position/joined area measuring unit 51.

The acceptability determining unit 37b determines the acceptability by comparing the size of the minimum required size of the molten-solidified portion 27 and the size of the molten-solidified portion 27 obtained by the molten-solidified portion detecting unit 54, resulting in automatic examination.

Hereunder, the operation of the three-dimensional ultrasonic inspection apparatus 10 will be described.

In order to obtain the ultrasonic test image of the joined area 15, which is the inspecting region (target region) of the object to be inspected, by means of the three-dimensional ultrasonic inspection apparatus 10, the ultrasonic transducer 11, which is a matrix sensor is activated.

The ultrasonic transducer 11 sequentially applies pulsed or continuous drive signals generated in the signal generating unit 12 to the matrix piezoelectric vibrators 20 one or plurality of pulses at a time and at a required timing, using the drive element selecting unit 13. When the piezoelectric vibrators 20 are selected by the drive element selecting unit 13 and the drive signals (electric signals) act to select the piezoelectric vibrators 20mn, the selected piezoelectric vibrators 20mn are subjected to piezoelectric transducing, and ultrasonic waves having required frequencies are produced.

The ultrasonic waves U produced by the piezoelectric vibrators 20mn enter the inspecting region (joined area) 15 of the object to be inspected 14 through the acoustic wave propagating liquid medium 23 with a required spreading. The ultrasonic waves U entered the inspecting region 15 of the object to be inspected 14 sequentially reach to boundary layers having different densities inside the object 14 and irradiated in a plane. A portion of the ultrasonic waves plane (two-dimensional)-irradiated inside the object 14 is reflected at the boundary layer, and the reflected wave enters the matrix sensor 11 through the acoustic wave propagating liquid medium 23 as a reflected echo and enters the piezoelectric vibrators 20.

The piezoelectric vibrators 20 in which the reflected echo entered, act as piezoelectric transducing elements, and output an electric signal depending on the magnitude of the reflected echo to the signal detecting circuit 16. Since a large number of piezoelectric vibrators 20mn are provided to the ultrasonic transducer 11 constituting the matrix sensor 11, the ultrasonic waves sequentially produced by the piezoelectric vibrators 20mn with different oscillation positions, sequentially reflected at the joined area (inspecting region) of the object 14, enter the matrix sensor 11 as reflected echoes, and are sequentially sent from the piezoelectric vibrators 20 of the matrix sensor 11 to the signal detecting circuit 16 as electric signals of the reflected echoes.

Thereafter, the electric signals of the reflected echoes sent to the signal detecting circuit 16 enter the signal processing unit 17, the electric signals of the reflected echoes are subjected to signal processing in the signal processing unit 17, and the three-dimensional imaging data is made by the parallel processor 33 of the joined area 15, which is the inspecting region of the object to be inspected and the three-dimensional image generating unit 34.

At that time, since the signal processing unit 17 is equipped with the parallel processor 33, and the electric signals of the reflected echoes input to the signal processing unit 17 are subjected to an arithmetic processing in parallel by the parallel processor 33, the rapid arithmetic processing can be performed in a short time.

The three-dimensional image generating unit 34 generates three plane images by seeing through the three-dimensional imaging data from three directions, which are a front direction viewed from the ultrasonic transducer 11 and two directions perpendicular to the front direction and each other and by projecting the largest value data of the imaging data superposing in the see-through directions of the three-dimensional imaging data in each three directions on a plane.

Since the imaging data of the sides perpendicular to the front includes a large number of information in the thickness direction of the plurality of plate-like objects to be inspected 14 having the joined area 15, and the reflection intensity from the bottom of the first plate-like structure 14a viewed from the transducer 11 is high in the non-joined area in which the plate-like objects are not joined together, the bottom position of the plate-like structure 14a can be determined. Meanwhile, since, in the area where the plurality of plate-like objects 14 are joined together, the transmittance of the ultrasonic wave is high, the position of the bottom unit 29 of the plurality of plate-like objects 14 can be determined as the area having the highest reflection intensity.

When the bottom imaging dada of the non-joined area 26, which is the imaging data in the front direction of the intermediate layer portion only, is extracted, since the difference in reflection intensity between the joined area 15 and the non-joined area 26 are large, the boundary between the joined area 15 and the non-joined area 26 clearly appears as the shape of a joined area contour. From the joined area contour data, the state of the joined area 15 in the intermediate layer portion of the plurality of plate-like objects to be inspected 14, which is the size and the center position of the joined area, can be determined. Moreover, since the weld defect portion 28 such as a blowhole generated in the molten-solidified portion 27 inside the joined area 15 also appears in the imaging data in the front direction of the intermediate layer portion, the size and the position of the weld defect portion 28 can be determined.

When the imaging dada of the bottom 29 of the entire plurality of plate-like objects to be inspected 14, which is the imaging data in the front direction of the bottom portion only, is extracted from the three-dimensional imaging data, the intensity distribution of the reflected echoes due to the difference between joined states in the joined area 15.

Although the bonding strength of the joined area 15 depends on the size of the molten-solidified unit 27 that is present in the joined area 15, it is known that the boundary between the mere joined area 15 and the molten-solidified portion 27 generated in the joined area 15 can be determined by the inflection point P of the reflection intensity distribution of the bottom portion 29 of the plate-like object 14.

Consequently, theoretically, since the contour data of the molten-solidified portion 27 in the joined area 15 can be obtained by subjecting the reflection intensity distribution of the bottom portion 29 of the plate-like object 14 to two differencing processings in the direction from the outer side of the molten-solidified portion 27 to the center position to calculate the inflection point 27 of the reflection intensity, the size and the position of the molten-solidified portion 27 can be measured.

However, practically, in some times, only non-continuous contour data can be obtained, and in some times, the size of the molten-solidified portion 27 cannot be measured in certain amounts and locations of the obtained continuous portions.

However, it is considered that the center of the joined area 15 and the center of molten-solidified portion 27 coincide with each other.

In the three-dimensional ultrasonic wave inspection apparatus 10, since the center position of the joined area 15 is measured from the size of the joined area 15 in the intermediate layer portion of the plurality of plate-like objects to be inspected 14, even if the contour data of the molten-solidified portion 27 is partially discontinuous data, it is possible to measure the size of the molten-solidified portion 27 by calculating continuous contour data from the discontinuous contour data using the center position.

Since the bonding strength of the joined area 15 depends on the size of the molten-solidified portion 27 existing in the joined area 15, the minimum required bonding strength for the plurality of plate-like joined area 15 is equivalent to the minimum required size of the molten-solidified portion 27.

Meanwhile, the minimum required bonding strength for the plurality of plate-like joined area 15, which is the minimum required size of the molten-solidified portion 27, is defined by the plate thickness "t" of the plate-like structure 14a of the object to be inspected 14.

Consequently, it is possible to determine whether the plurality of joined areas 15 of the object to be inspected 14 satisfy the minimum required bonding strength or not, by comparing the size of the molten-solidified portion 27 calculated from the plate thickness "t" of the plate-like structure 14a, which is a flat plate and the size of the molten-solidified portion 27 obtained as the measured result of the object to be inspected 14.

In addition, the three-dimensional ultrasonic wave inspection apparatus according to the present invention is not limited to that described in the above-mentioned embodiment, other various kinds of modifications may be considered.

One embodiment of the three-dimensional ultrasonic wave inspection apparatus adopts a configuration in which the signal processing unit 17 and display processing device 18 are included in the three-dimensional ultrasonic wave inspection apparatus 10 was used. However, the three-dimensional ultrasonic wave inspection apparatus can be provided by using independent computers. Moreover, the three-dimensional image generating unit 34 of the signal processing unit 17 may be included by shifting it into the display processing device 18.

The computers have functions of performing each processing in the present embodiment, and may have any configuration such as a computer apparatus composed of one device such as a personal computer, or a computer system where a plurality of computer apparatuses are connected in a network. Moreover, as for the computer, it is not limited to the personal computer, an arithmetic processing device included in communication devices and information processing devices, and a microcomputer may be included, and it is a generic term of devices and apparatuses enabling to perform the function of the present invention by means of program.

Moreover, the internal configuration of the display processing device 18 can be provided by using a software. The software may be a memory in a computer readable memory medium such as a flexible disk, and may be a type that is transferred on a network such as a LAN or an internet as a software (program) single body. In this case, by reading out the software (program) memorized in the memory medium and by downloading the software (program) from a site (server) on the LAN or the internet to install a hard disk, it is possible to perform processing in the computer.

In other words, as for the software (program) in the present invention, it is not limited to those which memorized in a memory medium independent to the computer, and a type distributed through a transmitting medium such as the LAN or the internet may be included.

In addition, as for the program, if it is memorized in a memory medium such as a memory, a flexible disk, a hard disk, an optical disk (CD-ROM, CD-R, DVD etc.), a magneto-optical disk (MO etc.), and a semiconductor memory in a computer readable manner, its language format and memory format may be taken freely.

Moreover, based on the instruction of a program installed in the computer, a portion of each processing for achieving the present embodiment may be performed by an MW (middleware) etc. such as an OS (operating system), a database-management software, a network software.

Further, as for the memory medium, it is not limited to media independent to the computer, and memory media where a program transmitted by the LAN or the internet etc. is downloaded and memorized or temporarily memorized, may be included. Moreover, the memory medium is not limited to one, and, when the processings in the present embodiment are performed using a plurality of media, the media may be also included in the memory media in the present embodiment, and the configuration of the media may be taken by any configuration.

According to the three-dimensional ultrasonic wave inspection apparatus 10, it is possible to provide a three-dimensional ultrasonic wave inspection apparatus enabling to improve accuracy of the internal inspection by means of ultrasonic wave, and automatic examination of the inspection.

Figure 3:
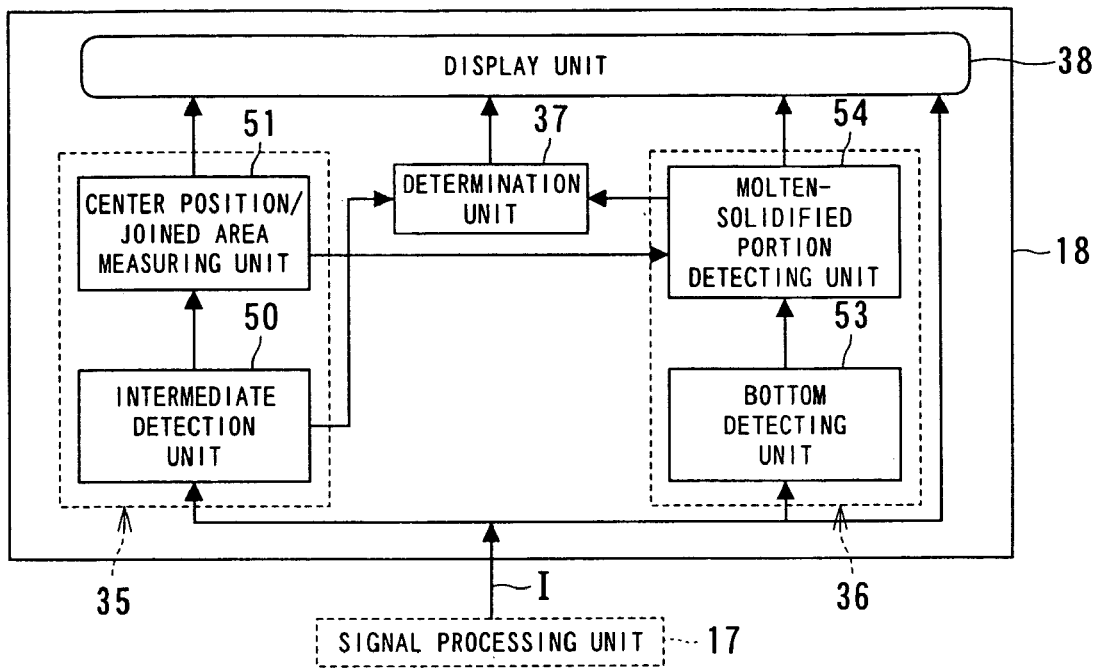
FIG. 3 is a block diagram showing the relationship between data processings in a display processing device equipped to the three-dimensional ultrasonic inspection apparatus according to the present invention.

Meanwhile, as mentioned hereinbefore, the present invention provides a sensing device for ultrasonic inspection according to the three-dimensional ultrasonic wave inspection apparatus having the above-mentioned configuration and action and shown in FIG. 3. Hereinafter, referring to FIGS. 10 to 14, embodiments thereof will be described. In addition, in the following descriptions, same or like reference numerals are added to members and elements of the three-dimensional ultrasonic wave inspection apparatus corresponding to those mentioned with reference to FIGS. 1 to 9.

First, a first embodiment of the sensing device for ultrasonic inspection used in the above-mentioned three-dimensional ultrasonic wave inspection apparatus 10 will be described with reference to FIG. 10.

The sensing device for ultrasonic inspection 100 according to the first embodiment, includes an ultrasonic sensor 11 in which a large number of piezoelectric elements 20 emitting and receiving ultrasonic waves are aligned and placed, and shoe means 21 for holding a liquid medium provided on the side of the surface for emitting and receiving the ultrasonic waves, which is the sensing surface of the ultrasonic sensor 11. The ultrasonic sensor 11 constitutes the transducers according to the embodiments represented by FIGS. 1 to 9, and the ultrasonic sensor 11 may be a matrix sensor in which a large number of piezoelectric elements 20 are disposed in "m" rows and "n" columns, or an array sensor in which a plurality of piezoelectric elements 20 are disposed in one column or in a cross shape.

The ultrasonic sensor 11 is configured to have an appearance having a cylindrical solid or a cylindrical hollow shape, and a tubular attachment 140 constituting shoe means 21 for holding a liquid medium is connected and unified to the ultrasonic sensor 11 through a screw connection, and held in a liquid-tight state by liquid-tight means 141 such as an O ring. In FIG. 10, although an example, in which the tubular attachment 140 is fitted around the inner ultrasonic sensor 11, was shown, a configuration in which the tubular attachment 140 is fitted inside the ultrasonic sensor 11 may be used.

A holding cap 143 is provided freely attachable and detachable to and from the tip side of the tubular attachment 140 through the screw connection, and a thin film 144 covering the tip opening of the tubular attachment 140 by the holding cap 143 in a liquid-tight state. In the holding cap 143, an opening exposing the thin film 144 is formed on the top of the cap, and the thin film 144 is sandwiched by the tubular attachment 140 and the holding cap 143 to be fixed and held. By fastening the holding cap 143, the thin film 144 is also fastened by the fastening operation of the holding cap 143, the thin film 144 is also fastened together to the tubular attachment 140.

In order to attach the thin film 144 to tubular attachment 140 in a liquid-tight state, the liquid-tight means 145 such as an O ring is caused to intervene between the tubular attachment 140 and the holding cap 143. Various kinds of modifications of the position to which the liquid-tight means 145 is attached, can be considered. The shoe means 21 is constituted by charging and filling water 147 as the ultrasonic wave propagating liquid medium in the tubular attachment 140 to which the thin film 144 is attached.

The thin film 144 of the shoe means 21 is manufactured as a soft medium using a rubber material or a resin material, and formed with a film thickness of a quarter or less of the wavelength λ of the ultrasonic wave propagating through the thin film 144, for example, an order of several μm to several dozens of μm. By setting the film thickness of the thin film 144 to be a quarter or less of the wavelength λ, for example, several μm or less, it is possible to prevent the degradation of the detection performance due to the wave pattern deformation, scattering, and multiple reflection of the ultrasonic wave transmitting through the thin film 144.

By providing the ultrasonic sensor 11 and the thin film 144 on one side and on the other side of the tubular attachment 140 in a liquid-tight state, respectively, and filling the inside of the tubular attachment 140 with water, the sensing device for ultrasonic inspection 100 is constituted.

The sensing device for ultrasonic inspection 100 is constituted by attaching the tubular attachment 140 to the ultrasonic sensor 11 through the screw connection and providing the holding cap 143 for pressing the thin film 44 to hold it to the tubular attachment 140, and before the tubular attachment 140 is filled with water 147, the ultrasonic wave emitting and receiving surface of the ultrasonic sensor 11 and the thin film 144 are kept in parallel with each other.

As for the assembling procedure of the sensing device for ultrasonic inspection 100, the tubular attachment 140 is slightly inserted into the ultrasonic sensor 11 by means of screwing, and then the inside of the tubular attachment 140 is filled with water 147 with the ultrasonic sensor 11 being downward.

Next, the thin film 144 is placed on the tubular attachment 140 so as to cover the tip opening of the tubular attachment 140, and the holding cap 143 is covered thereon to be fixed to the tubular attachment 140 by means of screwing. By screwing the holding cap 143, the thin film 144 is sandwiched between the holding cap 143 and the tubular attachment 140 in a liquid-tight state and fastened together.

Finally, the tubular attachment 140 is screwed into the ultrasonic sensor 11 with the thin film 144 being sandwiched by the holding cap 143. By screwing the tubular attachment 140, water pressure in the tubular attachment 140 rises, and thereby, the thin film 144 swells out from the opening 145 of the holding cap 143.

Due to the swelling-out effect, even if the surface shape of the object to be inspected 14 is not perfectly planar, and a curved surface such as an uneven surface is present, since the thin film 144 follows the surface shape of the object to be inspected 14, the thin film 144 can be efficiently and effectively is contacted to the surface of the object 14 to be inspected.

Consequently, in the sensing device for ultrasonic inspection 100, conventional shoe material and couplant are not required by filling water 147 between the ultrasonic sensor 11 and the thin film 144. Even if the surface of the inspecting region (a portion where the ultrasonic wave enters) of the object to be inspected 14 is not perfectly planar, it is possible to perform an image processing by the ultrasonic wave.

In addition, when unevenness is present on the surface of the inspecting region of the object 14, a gelled couplant having low volatility may be applied between the object 14 and the thin film 144 of the shoe means 21.

Reference numeral 148 denotes an electric cable or a signal cable connected to the ultrasonic sensor 11, which has function of sending a drive signal to the each piezoelectric element 20 of the ultrasonic sensor 11, and sending the electric signals of the reflected echoes received by the ultrasonic sensor 11 to the signal detecting circuit.

Figure 11:
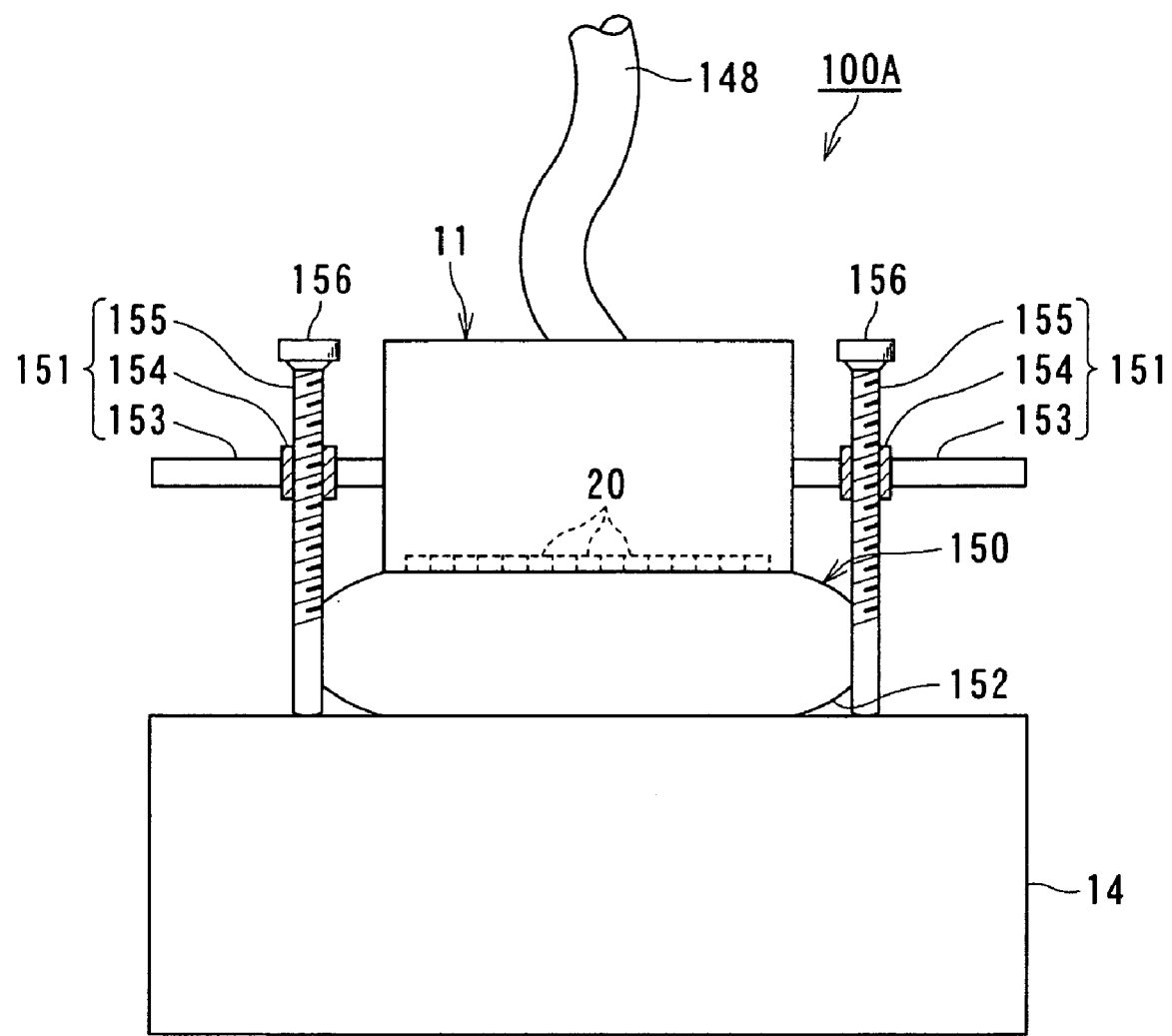
FIG. 11 is a schematic configuration view showing a second embodiment of the sensing device for ultrasonic inspection according to the present invention.

FIG. 11 is a view showing the second embodiment of the sensing device for ultrasonic inspection equipped with the three-dimensional ultrasonic wave inspection apparatus.

When explaining the sensing device for ultrasonic inspection 100A shown in FIG. 11, same reference numerals are added to the same components as those in the sensing device for ultrasonic inspection 100 of the first embodiment, and the description thereof will be omitted.

The sensing device for ultrasonic inspection 100A shown in the second embodiment, includes a ultrasonic sensor 11 where a large number of piezoelectric elements 20 are aligned and arranged in a matrix or an array, flexible shoe means 150 which is brought into close contact to the side of the surface of the ultrasonic sensor 11 for emitting and receiving the ultrasonic wave, and sensor position adjusting means 151 as elevating means for finely adjusting the ultrasonic sensor 11 so as to be freely advancable and retreatable with respect to the object to be inspected 14.

Figure 10:
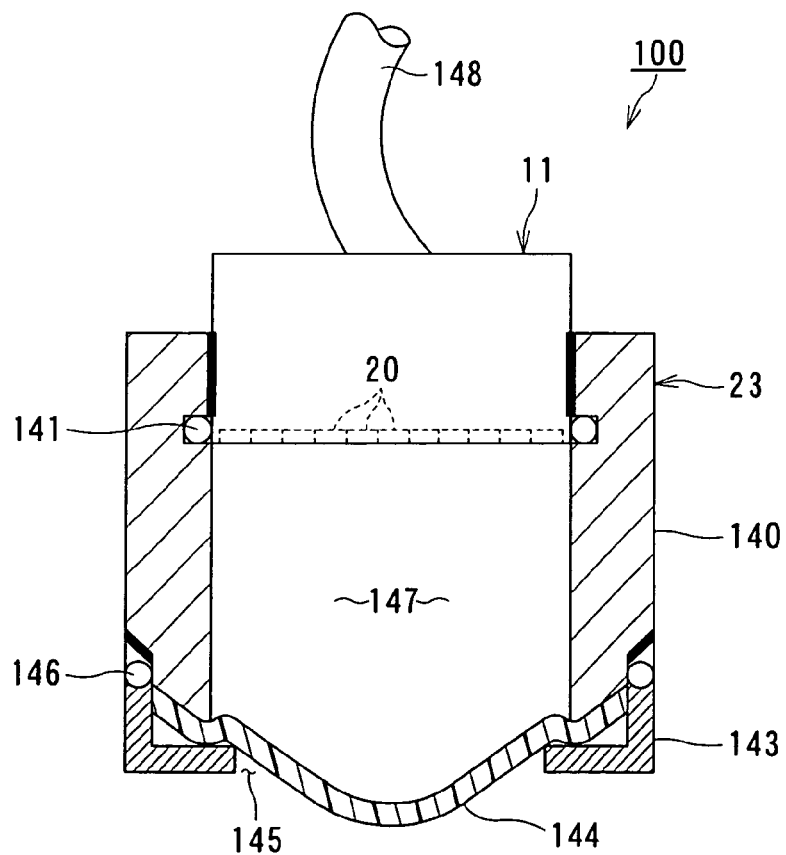
FIG. 10 is a schematic configuration view showing a first embodiment of a sensing device for ultrasonic inspection of the three-dimensional ultrasonic inspection apparatus according to the present invention.

Similar to the ultrasonic transducer shown in FIG. 10, the ultrasonic sensor 11 is constructed by a matrix sensor or an array sensor.

The flexible shoe means 150 provided on the ultrasonic wave emitting and receiving surface of the ultrasonic sensor 11 is constructed by a soft shoe member 152. On the surface of the soft shoe member 152, a gelled couplant having a low volatility is applied between the surface and the ultrasonic sensor 11 and between the surface and the object to be inspected 14.

The soft shoe member 152 is formed with a soft resin material such as a silicon rubber and polystyrene. When the flexible shoe member 150 is constructed by the soft shoe member 152, it is possible to directly fix the soft shoe member 152 by using bolts etc. In-the sensing device for ultrasonic inspection 100A, by containing the flexible shoe means 150 in sensor position adjusting means 151, which is a holding tool, it is possible to hold the flexible shoe means 150 in an immovable state in which the shoe shape is kept constant.

Moreover, the sensor position adjusting means 151 for advancing and retracting the ultrasonic sensor 11 with respect to the object to be inspected 14 includes a holding mount 153 for holding the ultrasonic sensor 11 from the outside, and leg bolts 155 which are connected to the vicinities of four corners of the holding mount 153 through a boss portion 154 by means of screwing and has a function as a holding and adjusting bolt. Three or more, for example four, of the leg bolts 155 are provided to the holding mount 153.

Further, it is possible to advance and retract (ascend and descend) the holding mount 153 with respect to the object to be inspected 14 in a finely adjustable manner, by subjecting bolt heads 156 to a rotational operation around the bolt shanklines, while pressing the leg bolts 155 to the object to be inspected 14, and to hold the holding mount 153 in its advancing and retracting state. The leg bolts 155 can be automatically operated by connecting the leg bolts 155 to drive motors (not shown) and individually and totally controlling the motor driving of each drive motor.

As for the sensing device for ultrasonic inspection 100A, by rotating the leg bolts 155 of the sensor position adjusting means 151 around the bolt shank-line, while pressing the leg bolts 155 to the object 14, the parallelism and distance (gap) between the ultrasonic sensor 11 and the object 14 can be finely adjusted, and it is accordingly possible to adjust the adhesive properties and the adhesive area between the object to be inspected 14 and the flexible shoe means 152 and the ultrasonic sensor 11 and the flexible shoe means 152.

In the flexible shoe means 150, in place of the soft shoe member 152 such as a silicon rubber, a flexible shoe member where a liquid medium such as water is filled between thin films made of a rubber or a resin, may be used.

Being sandwiched among three or more, for example, four leg bolts 155 of the sensor position adjusting means 151, the ultrasonic sensor 11, and the object 14, the flexible shoe means 152 is fixed, and thereby, hold in an immovable state, stably, unless being acted by an outer force. Consequently, the positional relation between the ultrasonic sensor 11 and the object to be inspected 14 becomes constant.

Since, in the sensing device for ultrasonic inspection 100A shown in FIG. 11, the flexible shoe means 152 is used as the flexible shoe means 150 at the side of the ultrasonic wave emitting and receiving surface of the ultrasonic sensor 11, even if the surface of the object to be inspected 14 is not planar, rather curved, it is possible to bring the soft shoe means 152 into close contact to the object to be inspected 14, stably, thus, enabling to cause the ultrasonic wave U to enter the object 14 stably and smoothly, without making an air layer between the soft shoe means 152 and the object to be inspected 14.

Figure 12:
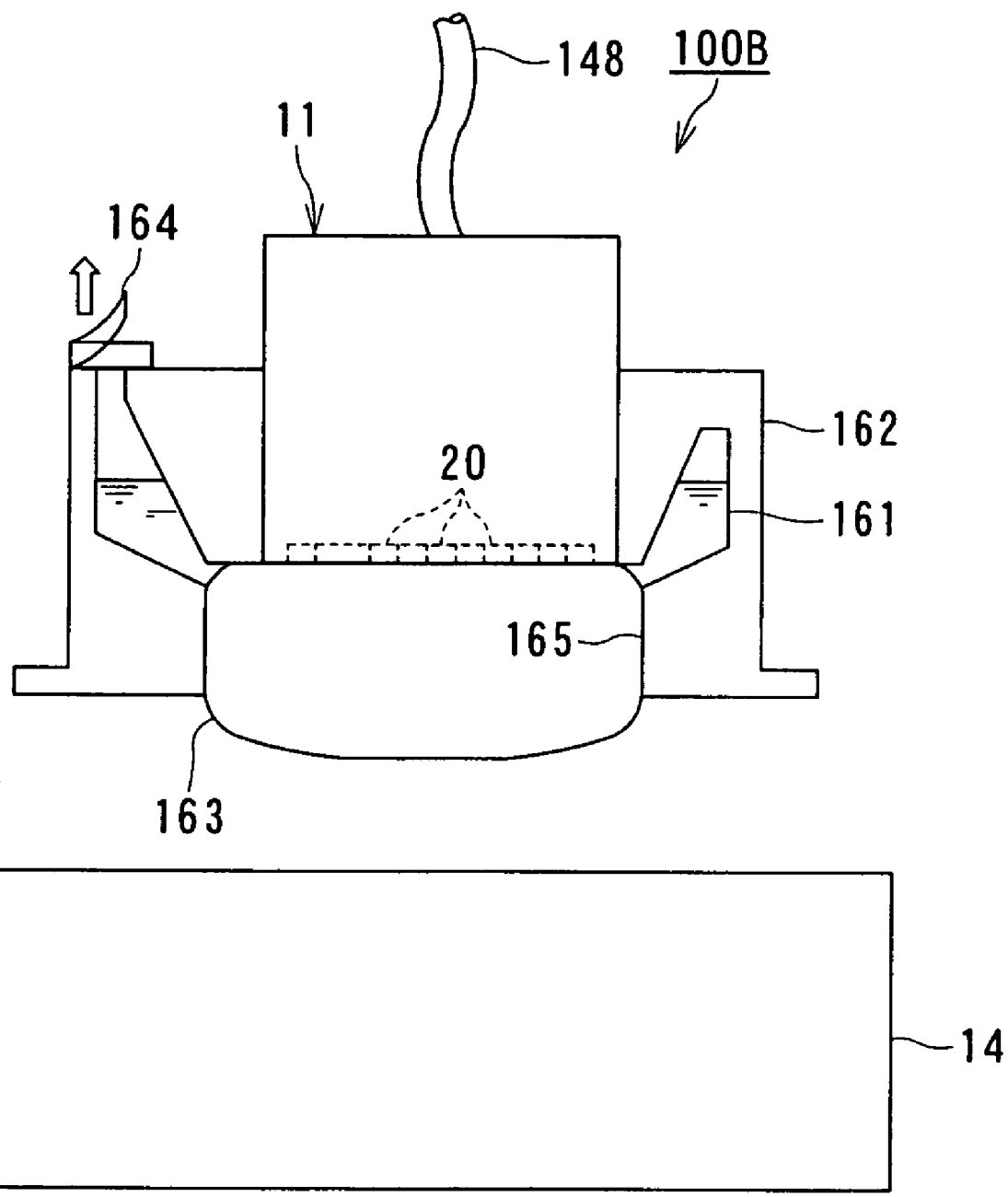
FIG. 12 is a schematic configuration view showing a third embodiment of the sensing device for ultrasonic inspection according to the present invention.

FIG. 12 is a view showing a third embodiment of the sensing device for ultrasonic inspection.

Same reference numerals are added to the units, members and the like corresponding to those described with reference to the sensing device for ultrasonic inspection of the first and second embodiments mentioned above, and the description thereof will be omitted.

The sensing device for ultrasonic inspection 100B shown in the third embodiment, includes: a ultrasonic sensor 11 in which a large number of piezoelectric elements 20 are aligned and arranged in a matrix or an array; shoe means for accumulating a medium (holding a liquid medium) 160 which holds water, which is an acoustic wave propagating liquid medium, on the side of the surface of the ultrasonic sensor 11 for emitting and receiving the ultrasonic wave as a sensing surface; and a sensor holder equipped with a water-tank 161 which is placed around the ultrasonic sensor 11, and a reservoir enabling to supply water to the shoe means for accumulating a medium 160 as the supersonic wave propagating liquid medium.

The shoe means for accumulating a medium 160 includes a spongy or porous flexible shoe member 163 which is provided on the side of sensing surface (surface for emitting and receiving the ultrasonic wave) of the ultrasonic sensor 11, and the shoe member 163 includes a large accumulating space enabling to accumulate sufficient amount of water (supersonic wave propagating liquid medium) between the ultrasonic sensor 11 and the object to be inspected 14.

Consequently, when the shoe member 163 is attached to the ultrasonic sensor 11, the shoe member 163 swells out largely from the supporting portion, which is a portion for connecting between the shoe member 163 and the water-tank 161 to the object 14.

Moreover, the shoe member 163 is supported so as to be wrapped with the torus-like or sleeve-like water tank 161. The water tank 161, which is a reservoir, is equipped with an air vent valve 164 for venting air in the tank on the top thereof. A sleeve-like or skirt-like tank guide of the water tank 161, covers the side surrounding the spongy or porous flexible shoe member 163. The water tank 161 is constructed together with the ultrasonic sensor 11, and always filled with water, by adjusting the over and short of water contained in the flexible shoe means 163.

It is possible to maintain a good propagation of the ultrasonic wave U by always filling water in the flexible shoe means 163.

Further, since the spongy or porous flexible shoe means 163 can be brought into contact to the curved shape on the surface of the object to be inspected 14, by filling the water supplied to the flexible shoe means 163 between the object 14 of the flexible shoe means 61, it is possible for the ultrasonic wave to effectively transmit inside of object 14, and for the reflected echo of the ultrasonic wave reflected from the boundary layer such as an inner defect of the object 14 to effectively transmit.

For this purpose, the water tank 161 is communicated with the top of the shoe member 163 so that the surface, which is a sensing surface of the ultrasonic sensor 11 for emitting and receiving the ultrasonic wave, is directly brought into contact with the flexible shoe member 162. An attaching unit (placing unit) 166 for attaching the sensor holder 162 holding the water tank 161 to the object to be inspected 14 is also formed so that the flexible shoe means 163 and the object 14 are brought into direct contact to each other.

The attaching unit 166 of the sensor holder 162 is formed so as to be parallel to the surface of the ultrasonic sensor 11 for emitting and receiving the ultrasonic wave, and constructed so that the surface of the ultrasonic sensor 11 for emitting and receiving the ultrasonic wave and the inspecting surface of the object to be inspected 14 are parallel with each other.

The assembling procedure and the effect of the sensing device for ultrasonic inspection 100B will be described hereunder.

In the sensing device for ultrasonic inspection 100B, the flexible shoe means 163 is attached to the ultrasonic sensor 11, and before abutting the shoe member 163 to the object to be inspected 14, water is sufficiently immersed in the shoe member 163.

When the ultrasonic sensor 11 is placed on the object 14, flexible shoe means 163 is fitted to the surface shape of the object 14, thereby, the water inside the shoe member 163 flows into the side of the water tank 161 by an pressed and deformed amount of the shoe member 163 filled with water between the object to be inspected 14 and the ultrasonic sensor 11.

Moreover, since the water tank 161 is formed so as to have a passage structure directing from the flexible shoe means 163 to upward, air bubbles occurred in the shoe member 163 between the ultrasonic sensor 11 and the object 14 are guided to the water tank 161.

When the ultrasonic wave is directed to the object to be inspected 14, the pressure in the water tank 161 increases due to the water and air bubbles entering the water tank 163. However, the pressure increase can be suppressed by opening the air vent valve 164. The air vent valve 164 is closed when the pressure inside the water tank becomes equal to atmospheric pressure.

Since, the sensing device for ultrasonic inspection 100B is equipped with the flexible shoe means 163 filled with water between the ultrasonic sensor 11 and the object 14, and the internal inspection of the object 14 is performed using the ultrasonic wave, by performing an ultrasonic wave inspection action with the water held by the flexible shoe means 163 being filled, and in the internal inspection, image processing is performed by producing the ultrasonic wave by the ultrasonic sensor 11.

By the operation of the sensing device for ultrasonic inspection 100B, when the ultrasonic inspection action of the internal construction of the inspecting region of the object to be inspected 14 is finished, the ultrasonic sensor 11 is moved to a next inspecting region. When the ultrasonic sensor 11 is moved, a continuous image processing can be performed, by releasing the ultrasonic sensor 11 from the object to be inspected 14, moving it to a next object to be inspected, and thereafter, pressing the sensing device for ultrasonic inspection 100B to the next object. Since the sensing device for ultrasonic inspection 100B is equipped with the shoe member filled with water, it is not required to apply the couplant, and the couplant is not required.

In the sensing device for ultrasonic inspection 100B, by using the spongy flexible shoe means 163 attached to the side of the ultrasonic wave emitting and receiving surface of the ultrasonic sensor 11, even when a plurality of areas to be inspected are subjected to image processing, the ultrasonic inspection can be performed by merely pressing the shoe member 163 of the ultrasonic sensor 11 against the object to be inspected 14, thus enabling continuous ultrasonic image processing.

Figure 13:
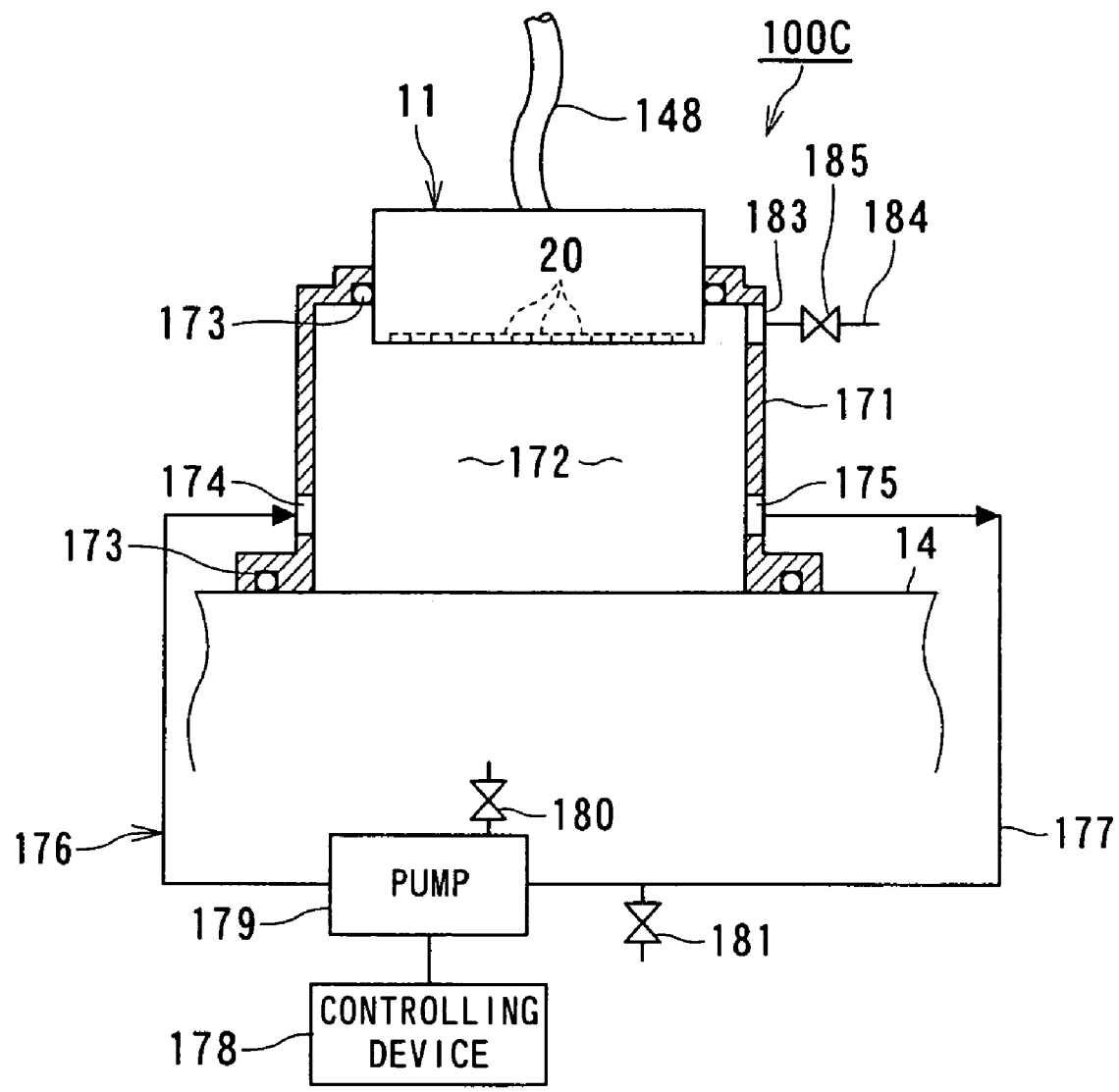
FIG. 13 is a schematic configuration view showing a fourth embodiment of the sensing device for ultrasonic inspection according to the present invention.

FIG. 13 is a schematic view simply explaining a forth embodiment of the sensing device for ultrasonic inspection.

A sensing device for ultrasonic inspection 100C shown in this embodiment includes: a ultrasonic sensor 11, in which a large number of piezoelectric elements 20 are aligned and arranged in a matrix or an array; and water-tank-type shoe means 170 provided on the side of the surface, which is a sensing surface of the ultrasonic sensor 11 for emitting and receiving the ultrasonic wave. The ultrasonic sensor 11 is not different from the ultrasonic sensors used in the first to fourth embodiments.

The water-tank-type shoe means 170 is equipped with a skirt-like or sleeve-like tank 171 attached on the surface surrounding the ultrasonic sensor 11, and the tank 171 is mounted on the measuring region of the object to be inspected 14 in a liquid-tight manner. The water tank is constructed by charging water 172 inside the tank 171 as the acoustic wave propagating liquid medium, with the tank 171 being mounted on the object to be inspected 14 in a liquid-tight manner.

In order to mount the tank 171 on the object 14 in a liquid-tight manner, liquid-tight means 173 such as an O-ring is provided on the placing surface of the tank 171. The liquid-tight structure may also constituted by using a sucker by providing the sucker on the placing surface of the tank 171 instead of the liquid-tight means 173. Moreover, in order to attach the tank 171 to the ultrasonic sensor 11 in a liquid-tight manner, liquid-tight means 173 such as the O-ring may be provided similarly.

The tank 171 of the water-tank shoe means 170 is equipped with a water supply port 174 and a drain port 175 on the side of the tank, and circulation-type medium (water) supplying means 176. The circulation-type medium supplying means 176 has a closed loop 177 of the liquid medium (water) extending from the drain port 175 to the inflow port 174, and at the middle of the water loop 177, a pump 179 drive-controlled by a controlling device 178 is provided. Further, reference numeral 180 denotes a supply valve provided to a liquid medium supply pipe (water supply pipe) at the suction side of the pump 179, and reference numeral 181 denotes a drain valve provided to a drain pipe branched from the water loop 177 at the inflow side of the pump.

Moreover, on the top portion of the tank of the water shoe means 170, the surface of the ultrasonic sensor 11 for emitting and receiving the ultrasonic wave is provided so as to protrude in the tank, an air vent pipe 184 is connected to an air vent port 183 formed on the upper side than the surface for emitting and receiving the ultrasonic wave, and an air vent valve 185 is provided to the air vent pipe 184.

In the sensing device for ultrasonic inspection 100C, the surface of the ultrasonic sensor 11 for emitting and receiving the ultrasonic wave and the attaching portion (placing portion) of the tank 171 to the object 14 are formed in parallel with each other. This enables to maintain the distance and the parallelism between the front (the surface for emitting and receiving the ultrasonic wave) of the ultrasonic sensor 11 and the object to be inspected 14.

Furthermore, since the tank 171 is entirely opened, when the tank 171, to which the ultrasonic sensor 11 is attached, is placed on the object to be inspected 14, the water 172 in the tank 171 is directly brought into contact to the object 14 and the surface of the ultrasonic sensor 11 for emitting and receiving the ultrasonic wave, so that even when the water tank is filled with water by the liquid-tight means 173, 173, the water 172 in the tank does not leak from the water tank.

In the sensing device for ultrasonic inspection 100C, since the ultrasonic sensor 11 is equipped with the tank 171 constructing the water tank, which is constructed by pressing the ultrasonic sensor 11 integrated to the tank 171 against the object to be inspected 14, even when water is sent in the tank, the leakage of the water can be prevented.

The ultrasonic sensor 11, with tanks constructing the water tank, is placed on the inspecting region of the object to be inspected 14, and the air vent valve 185 of the tank 171 is opened, while pressing force to the ultrasonic sensor 11. The drain valve 181 is closed with the air valve being opened, and the water for flowing in the water loop 177 is poured in the loop 177 by opening the water supply valve 180 of the pump. While pouring water in the water loop 177, which is guided from the water supply valve 180 of the pump to the water loop 177, the pump 179 is controlled by the control device 178.

The pump 179 is driven, and the operation of the pump 179 is stopped by closing the air vent valve 184 after confirming that the water 172 is filled between the ultrasonic wave emitting/receiving portion of the ultrasonic sensor 11 and the object 14 and confirming the absence of the air bubbles in the water 172 of the tank 171.

The sensing device for ultrasonic inspection 100C is started after the inside of the water tank constructed by the tank 171 and the surface of the object to be inspected 14 is filled with water. The ultrasonic wave is emitted and received from each piezoelectric element 20 of the ultrasonic sensor 11 by the operation of the sensing device for ultrasonic inspection 100C, the inner structure of the object to be inspected 14 is inspected by using the ultrasonic wave, and the image processing is performed.

At that time, the ultrasonic wave emitting/receiving unit of the ultrasonic sensor 11 and attaching unit of the tank 171 for the object 14 are constructed to be in parallel with each other, similar to the case when a conventional block-like parallel plane shoe member is used. Therefore, the ultrasonic wave is caused to enter perpendicular to the object to be inspected 14.

After the image processing by the ultrasonic wave is finished, at which the ultrasonic wave from the ultrasonic sensor 11 is caused to enter the object to be inspected 14, and the electric signal of the reflected echo is processed by receiving the reflected echo using the ultrasonic sensor 11, a water draining processing is performed, in which the drain valve 181 of the water loop 177, and the air vent valve 185 of the water-tank are opened, the pump 170 is operated, and the water in the water tank and the water loop 177 is drained.

After the water draining processing is finished, the ultrasonic sensor 11 is moved to the next portion to be inspected, and the ultrasonic image by the ultrasonic inspection is obtained.

According to the sensing device for ultrasonic inspection 100C, by filling water into the water-tank equipped to the ultrasonic sensor 11 by the operation of the pump 179, the conventional block-like shoe member and the couplant become to be unnecessary. Since the tank 171 constructing the water tank is opened to the side of the object to be inspected 14, when the water 172 is filled in the water-tank, the water 172 having good ultrasonic propagating characteristics is directly brought into contact with the surface of the inspecting region of the object 14. Accordingly, even when the surface of the object 14 is not perfectly planar, the image processing can be performed by using the ultrasonic wave without using the couplant.

Figure 14:
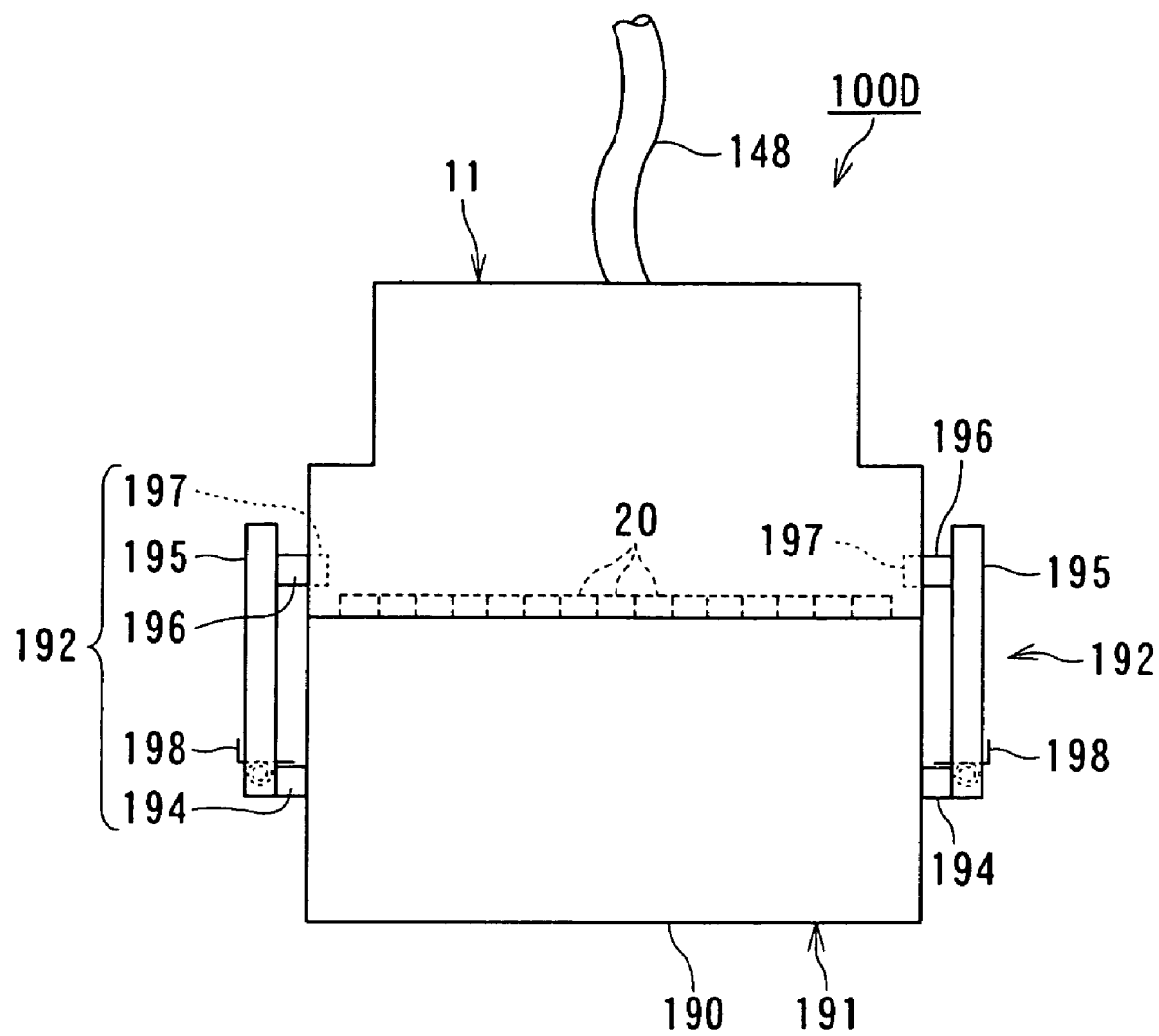
FIG. 14 is a schematic configuration view showing a fifth embodiment of the sensing device for ultrasonic inspection according to the present invention.

FIG. 14 is a schematic configuration view showing a fifth embodiment of the sensing device for ultrasonic inspection of the present invention.

The sensing device for ultrasonic inspection 100D shown in the fifth embodiment, includes: a ultrasonic sensor 11 in which a large number of piezoelectric elements 20 are aligned and arranged in a matrix or an array; shoe means 191 formed with a block-like shoe member 190 brought into close contact with the side of the ultrasonic wave emitting/receiving surface of the ultrasonic sensor 11; and one-touch-type attaching means 192 for detachably attaching the shoe means 191 to and from the side of the ultrasonic wave emitting/receiving surface of the ultrasonic sensor 11. The shoe member of the shoe means 191 is formed with a material having excellent acoustic wave propagating characteristics such as reinforced polystyrene, an epoxy resin, or ceramics, in a parallel plane shape so that the ultrasonic wave emitting/receiving surface and the opposite surface are parallel with each other.

The one-touch-type attaching means 192 has an attaching tool 194 to be attached to both the facing side walls of the shoe member 191 from the outside, lock member 195 rotatably attached to the attaching tool 194, and spring means 198 for biasing a hook 196 provided on the side of free end of the lock member 195 to the side of an engaging hole 197 of the ultrasonic sensor 11 by a spring. By engaging the engaging hook 196 of the lock member 195 with the engaging hole 197, the lock member is fixed, and the shoe member 191 is attached by one-touch and fixed to the ultrasonic wave emitting/receiving surface of the ultrasonic sensor 11 so as to be brought into contact with the surface. Instead of the engaging hole 197 formed in the ultrasonic sensor 11, a fixing tool engageable to the engaging hook 196 may be attached to the ultrasonic sensor 11.

In the sensing device for ultrasonic inspection 100D, by detachably attaching the block-like shoe member 190 having a parallel plane to the ultrasonic sensor 11 using the one-touch-type attaching means 192, the shoe member 190, which is shoe means 191, can be simply attached to and detached from the ultrasonic sensor 11 by using the one-touch-type attaching means 192.

According to the sensing device for ultrasonic inspection 100D, the shoe means 191 can be detached by one-touch, and accordingly, even if air bubbles enter on the sensing surfaces of the shoe member 190 and the ultrasonic sensor 11 and the sensing surface of the object to be inspected, it is easily possible for the sensing device for ultrasonic inspection 100D to be adjusted, by detaching the shoe means 191 from the ultrasonic sensor 11 and applying a gelled couplant having low volatility on the surface of the shoe member 190 of the shoe means 191, so that air bubbles does not enter the sensing device for ultrasonic inspection 100D.

In addition, the sensing device for ultrasonic inspection described in FIGS. 10 to 14, is not limited to the three-dimensional ultrasonic wave inspection apparatus having configurations described in FIGS. 1 to 9, and it can also be applied to a three-dimensional ultrasonic wave inspection apparatus having another configuration.

The invention claimed is:

1. A three-dimensional ultrasonic inspection apparatus comprising:
   a sensing device for ultrasonic inspection including a transducer as an ultrasonic sensor having a plurality of piezoelectric vibrators disposed in a matrix or an array;
   a drive element selecting unit for sequentially selecting piezoelectric vibrators from the plurality of piezoelectric vibrators constituting the ultrasonic transducer to produce an ultrasonic wave;
   a signal detecting circuit for causing the ultrasonic wave produced by the piezoelectric vibrator selected by the drive element selecting unit to propagate through an acoustic wave propagating medium and enter a joined area of an object to be inspected for receiving a reflected echo from the joined area, and for detecting an electric signal corresponding to the reflected echo from the joined area;
   a signal processing unit for subjecting the electric signal detected by the signal detecting circuit to signal processing, and generating three-dimensional imaging data by causing the electric signal to correspond to a mesh element partitioned in a three-dimensional imaging region set inside the object to be inspected; and
   a display processing device for displaying the detection results and three-dimensional image data from the signal processing unit, while detecting a size and a position of a molten-solidified portion, and a size and a position of a weld defect of the joined area from intensity distribution of the three-dimensional imaging data generated by the signal processing unit,
   wherein the display processing device includes:
   a bottom portion data processing unit for detecting the size and position of a molten-solidified portion from a strength distribution of three-dimensional imaging data of a bottom of the joined area of the object to be inspected generated by the signal processing unit;
   an intermediate portion data processing unit for detecting presence or absence and the size of a molten defect of the joined area from the strength distribution of the three-dimensional imaging data of an intermediate joined area of the object to be inspected;
   a determination unit for comparing detected results obtained by the bottom portion data processing unit and the intermediate portion data processing unit with determination reference values of the presence or absence and the size and position of the determined molten-solidified portion, and determining the acceptability of the object to be inspected based on the comparing; and
   a display unit for displaying the results obtained by the bottom portion data processing unit, the intermediate portion data processing unit and the determination unit, and displaying the three-dimensional imaging data generated by the signal processing unit.

2. The three-dimensional ultrasonic inspection apparatus according to claim 1, wherein the intermediate portion data processing unit of the display processing device includes:

an intermediate detection unit for generating a transmitting plane image of an intermediate joined surface by extracting three-dimensional imaging data of the intermediate portion of the joined area of the object to be inspected from the three-dimensional imaging data generated by the signal processing unit and for measuring the plate thickness; and a center position/joined area measuring unit for measuring the center position of the intermediate joined area, the size and the position of the joined area, and the size and the position of the weld defect such as a blowhole.

3. The three-dimensional ultrasonic inspection apparatus according to claim 1, wherein the bottom portion data processing unit of the display processing device includes:

a bottom detecting unit for generating a transmitting plane image by extracting three-dimensional imaging data of the bottom of the object to be inspected from the three-dimensional imaging data generated by the signal processing unit; and a molten-solidified portion detecting unit for measuring the size and the position of the molten-solidified portion from the transmitting plane image generated by the bottom detecting unit and the center position determined by the center position/joined area measuring unit.

4. The three-dimensional ultrasonic inspection apparatus according to claim 1, wherein the display processing device includes:

a determination unit for performing acceptability determination by comparing an acceptance standard obtained from a plate thickness of the object to be inspected obtained by the intermediate detection portion of the intermediate portion data processing unit, with the size and the position of the molten-solidified portion obtained by the molten-solidified portion detecting unit of the bottom data processing unit; and a display unit for displaying determination results in which a state of the joined area obtained by a center position/joined area determining unit of the bottom data processing unit and the state of the molten-solidified portion obtained by the determination unit are compared and displaying three-dimensional imaging data generated at the signal processing unit.

5. The three-dimensional ultrasonic inspection apparatus according to claim 1, wherein the intermediate data processing unit of the display processing device includes an intermediate detection unit including:

a surface/intermediate position detecting unit for detecting the surface position and the joined area position from three-dimensional imaging data generated by the signal processing unit;

a plate thickness measuring unit for measuring a plate thickness from data of a surface position and the joined area position generated by the surface/intermediate position detecting unit; and an intermediate position plane surface image generating unit for generating a transmitting plane surface image of the intermediate position from the intermediate position data obtained by the surface/intermediate position detecting unit and the three-dimensional imaging data generated by the signal processing unit.

6. The three-dimensional ultrasonic inspection apparatus according to claim 1, wherein the intermediate portion data processing unit of the display processing device includes a center position/joined area measuring unit, the center position/joined area measuring unit including:

a joined area contour determining unit for determining contours of the joined area from the intermediate position transmitting plane image generated by the intermediate detection unit;

a center position determining unit for determining the center position of the joined area from the contour data of the joined area obtained by the joined area contour determining unit; and a joined area measuring unit for measuring the size of the joined area from the contour data of the joined area obtained by the joined area contour determining unit.

7. The three-dimensional ultrasonic inspection apparatus according to claim 1, wherein the bottom portion data processing unit of the display processing device includes a bottom detecting unit, the bottom detecting unit including:

a dent portion/bottom position detecting unit for detecting a concave position representing a dent unit of the joined area and the bottom position of the object to be inspected from the three-dimensional imaging data generated by the signal processing unit;

a joined area thickness measuring unit for measuring the thickness of the joined area from the data of the concave portion/bottom position obtained by the dent portion/bottom position detecting unit; and a bottom position plane image generating unit for generating bottom position transmitting plane image from the data of concave portion /bottom position obtained by the dent portion/bottom position detecting unit and the three-dimensional imaging data generated by the signal processing unit.

8. The three-dimensional ultrasonic inspection apparatus according to claim 1, wherein the bottom portion data processing unit of the display processing device includes a molten-solidified portion detecting unit, the molten-solidified portion detecting unit including:

a strength distribution generating unit for generating a ultrasonic wave intensity distribution image from the bottom position transmitting plane image generated by the bottom detecting unit of the center position of the joined area obtained by a center position/joined area measuring unit of the intermediate portion data processing unit;

a smoothing processing unit for subjecting the ultrasonic wave intensity distribution image generated by the strength distribution generating unit to smoothing processing;

a primary differencing processing unit for subjecting the smoothed bottom position transmitting plane image to primary differencing in the direction from an outside to a center position;

a secondary differencing processing unit for subjecting the bottom position transmitting plane image subjected to primary differencing in the primary differencing processing unit to secondary differencing in the direction from an outside of the molten-solidified portion to a center position;

a molten-solidified portion identifying unit for identifying the molten-solidified portion of the joined area from inflection point data of the bottom position transmitting plane image subjected to secondary differencing; and a molten-solidified portion measuring unit for measuring the size of the molten-solidified portion from the molten-solidified portion data identified by the molten-solidified portion identifying unit.

9. The three-dimensional ultrasonic inspection apparatus according to claim 1, wherein the display processing device includes a determination unit for determining the acceptability of the joined state of the joined area, the determination unit including:

an acceptance standard generating unit for calculating a required size of the molten-solidified portion from a plate thickness "t" measured by the center position/joined area measuring unit of the intermediate portion data processing unit; and an acceptability determining unit for comparing a required size of the molten-solidified portion generated by an acceptance standard generating unit with the size of the molten-solidified portion measured by the molten-solidified portion detecting unit of the bottom portion data processing unit, and determining the acceptability of the joined state of the joined area.

10. The three-dimensional ultrasonic inspection apparatus according to claim 1, wherein the sensing device for ultrasonic inspection includes:

an ultrasonic sensor as a transducer having a plurality of piezoelectric elements for emitting and receiving the ultrasonic wave arranged in a matrix or an array; and a shoe member for holding a liquid medium which is provided on the side of the sensing surface of the ultrasonic sensor, the shoe member including: a tubular attachment provided to be freely attachable and detachable to and from the ultrasonic sensor through screw connection; a holding cap for fastening a thin film covering a top end opening of the attachment together with the attachment; and an acoustic wave propagating liquid medium filling the tubular attachment, and the thin film having a configuration swelling out from an opening of the holding cap and having flexibility.

11. The three-dimensional ultrasonic inspection apparatus according to claim 10, wherein the acoustic wave propagating liquid medium is water, and the thin film has a thickness equal to or less than a quarter of the wavelength λ of the ultrasonic wave propagating through the thin film.

12. The three-dimensional ultrasonic inspection apparatus according to claim 1, wherein the sensing device for ultrasonic inspection includes:

an ultrasonic sensor as a transducer having a plurality of piezoelectric elements for emitting and receiving the ultrasonic waves arranged in a matrix or in an array;

a flexible shoe member provided on a side of the sensing surface of the ultrasonic sensor; and a sensor position adjusting member for containing the flexible shoe member and holding the ultrasonic sensor so as to be advanced and retracted with respect to the object to be inspected.

13. The three-dimensional ultrasonic inspection apparatus according to claim 12, wherein the flexible shoe member includes a soft shoe member having an excellent ultrasonic wave propagating property, and the sensor position adjusting member includes a holding frame for holding the ultrasonic sensor and supporting/adjusting bolts connected to the holding frame through screw connection at least at three points near the ultrasonic sensor, and the position of the ultrasonic sensor is adjusted by rotating the supporting/adjusting bolts around a bolt shank-line.

14. The three-dimensional ultrasonic inspection apparatus according to claim 1, wherein the sensing device for ultrasonic inspection includes:

an ultrasonic sensor as a transducer having a plurality of piezoelectric elements for emitting and receiving the ultrasonic wave arranged in a matrix or an array;

a shoe member for holding a liquid medium provided on a side of a sensing surface of the ultrasonic sensor; and a sensor holder having a medium reservoir supplying an ultrasonic wave propagating liquid medium to the shoe member.

15. The three-dimensional ultrasonic inspection apparatus according to claim 14, wherein the shoe member for holding a liquid medium includes: a spongy or porous flexible shoe member; and an ultrasonic wave propagating liquid medium that is poured by freely falling from the liquid medium reservoir in the shoe member to be accumulated and held in the shoe member.

16. The three-dimensional ultrasonic inspection apparatus according to claim 14, wherein, when equipped with an air vent valve on the top thereof, a reservoir includes a sleeve-like or skirt-like tank guide covering a peripheral side surface of the flexible shoe member.

17. The three-dimensional ultrasonic inspection apparatus according to claim 1, wherein the sensing device for ultrasonic inspection includes:

an ultrasonic sensor as a transducer with a plurality of piezoelectric elements for emitting and receiving the ultrasonic wave being arranged; and a water-tank-type shoe member provided on a side of a sensing surface of the ultrasonic sensor, the shoe member including a reservoir for the ultrasonic wave propagating liquid medium which is constituted by a tank holding the ultrasonic sensor at the top of the tank and the object to be inspected placed so as to cover the bottom opening of the tank in a fluid-tight manner.

18. The three-dimensional ultrasonic inspection apparatus according to claim 17, wherein, the water-tank-type shoe member includes: a circulation-type liquid medium supplying member for circulating the ultrasonic wave propagating liquid medium in the tank; and an air vent valve for venting air from a side of the top the tank.

19. The three-dimensional ultrasonic inspection apparatus according to claim 1, wherein the sensing device for ultrasonic inspection includes:

an ultrasonic sensor as a transducer having a plurality of piezoelectric elements for emitting and receiving the ultrasonic wave which are arranged in a matrix or an array;

a shoe member provided on a side of a sensing surface of the ultrasonic sensor; and a one-touch-type attaching member for detachably attaching the ultrasonic sensor to the ultrasonic sensor by one touch, wherein the shoe member is brought into close contact with the ultrasonic sensor and held against the ultrasonic sensor by the one-touch-type attaching member.

20. A sensing device for ultrasonic inspection comprising:

an ultrasonic sensor as a transducer, in which a plurality of piezoelectric elements for emitting and receiving an ultrasonic wave are arranged in a matrix or an array;

a shoe member provided on a side of a sensing surface of the ultrasonic sensor; and a one-touch-type attaching member detachably attached to the ultrasonic sensor by one touch, wherein the one-touch-type attaching member includes an attachment to be mounted from an outside to both side walls opposing to the shoe member, a lock member supported to be rotatable to the attachment, an engaging hook provided at a free end side of the lock member, and a fixture provided for the ultrasonic sensor so as to be engageable with the engaging hook, and the shoe means is brought into close contact with the ultrasonic sensor and held against the ultrasonic sensor by the one-touch-type attaching member.

* * * * *